(12) United States Patent
Picataggio et al.

(10) Patent No.: US 7,259,255 B2
(45) Date of Patent: Aug. 21, 2007

(54) GLYCERALDEHYDE-3-PHOSPHATE DEHYDROGENASE AND PHOSPHOGLYCERATE MUTASE PROMOTERS FOR GENE EXPRESSION IN OLEAGINOUS YEAST

(75) Inventors: Stephen K. Picataggio, Landenberg, PA (US); Quinn Qun Zhu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 407 days.

(21) Appl. No.: 10/869,630

(22) Filed: Jun. 16, 2004

(65) Prior Publication Data

US 2005/0014270 A1    Jan. 20, 2005

Related U.S. Application Data

(60) Provisional application No. 60/482,263, filed on Jun. 25, 2003.

(51) Int. Cl.
*C07H 21/04* (2006.01)
*C12N 12/81* (2006.01)
*C12N 1/00* (2006.01)

(52) U.S. Cl. .............. 536/24.1; 435/320.1; 435/69.1; 435/255.1

(58) Field of Classification Search ................ None
See application file for complete search history.

(56) References Cited

U.S. PATENT DOCUMENTS

| | | | |
|---|---|---|---|
| 4,937,189 A | 6/1990 | Davidow et al. | |
| 6,265,185 B1 | 7/2001 | Muller et al. | |
| 6,451,565 B1 | 9/2002 | Rabenhorst et al. | |

FOREIGN PATENT DOCUMENTS

| | | |
|---|---|---|
| DE | 227448 | 9/1985 |
| DE | 259637 | 8/1988 |
| DE | 267999 | 5/1989 |
| DE | 275480 | 1/1990 |
| DE | 279267 | 5/1990 |
| DE | 285370 | 12/1990 |
| DE | 285372 | 12/1990 |
| EP | 0005277 B1 | 1/1982 |
| EP | 220864 | 5/1987 |
| EP | 578388 | 1/1994 |
| EP | 770683 | 5/1997 |
| EP | 832258 | 4/1998 |
| FR | 2734843 | 12/1996 |
| JP | 09252790 | 9/1997 |
| PL | 160027 | 1/1993 |
| RU | 2090611 | 9/1997 |
| RU | 2096461 | 11/1997 |
| SU | 1454852 | 1/1989 |
| WO | WO 2001083773 A1 | 11/2001 |
| WO | WO 2001088144 A1 | 11/2001 |

OTHER PUBLICATIONS

Thomas Juretzek et al., Comparison of Promoters Suitable for Regulated Overexpression of beta-Galactosidase in the Alkane-Utilizing Yeast Yarrowia lipolytica, Biotechnol. Bioprocess Eng., vol. 5:320-326, 2000.
U.S. Appl. No. 10/840,579, filed May 6, 2004, Dupont.
Ratledge, Microbial Oils and Fats: An Assessment of Their Commercial Potential, C., Prog. Ind. Microbiol. vol. 16: pp. 119-206, 1982.
Bitter,Expression of heterologous genes in *Saccharomyces cerevisiae* from vectors utilizing the glyceraldehydes-3-phosphate dehydrogenase gene promoter, G.A. et al., Gene 32(3): pp. 263-274, 1984.
Rodicio et al., Transcriptional control of yeast phosphoglycerate mutase-encoding gene, Gene, 125(2), 125-133, 1993.
Blanchin-Roland et al., Two Upstream Activation Sequences Control the Expression of the XPR2 Gene in the Yeast Yarrowia lipolytica, Mol. Cell Biol. vol. 14(1): pp. 327-338, 1994.

*Primary Examiner*—Scott Priebe
*Assistant Examiner*—Maria Marvich

(57) ABSTRACT

The promoter regions associated with the *Yarrowia lipolytica* glyceraldehyde-3-phosphate dehydrogenase (gpd) and phosphoglycerate mutase (gpm) genes have been found to be particularly effective for the expression of heterologous genes in oleaginous yeast. The promoter regions of the invention have been shown to drive high-level expression of genes involved in the production of ω-3 and ω-6 fatty acids.

1 Claim, 14 Drawing Sheets

A: *Saccharomyces cerevisiae* (SEQ ID NO:1; GenBank Accession No. CAA24607)
B: *Schizosaccharomyces pombe* (SEQ ID NO:2; GenBank Accession No. NP_595236)
C: *Aspergillus oryzae* (SEQ ID NO:3; GenBank Accession No. AAK08065)
D: *Paralichthys olivaceus* (SEQ ID NO:4; GenBank Accession No. BAA88638)
E: *Xenopus laevis* (SEQ ID NO:5; GenBank Accession No. P51469)
F: *Gallus gallus* (SEQ ID NO:6; GenBank Accession No. DECHG3)

```
                                                                              A
  1 KYDSTHGRFKCKVEAKDGGLII DGKHI CVFGERDPSNI PWGKAGADYVVE                     B
 48 KYDSTHGRFEGSVETKGGKLVI DGHSI DVHNERDPANI KVSASGAEYVI E                    C
 46 KYDSTHGHFKGTVKAENGKLVI NGHAI TI FQERDPSNI KWADAGAEYVVE                    D
 46 KYDSTHGRFKGTVKAENGKLII NDQVI TVFQERDPSSI KWGDAGAVYVVE

A
 51 STGVFTGKEAASAHL KGGAKKVI I SAPSGDAPMFVVGVNL DAYKPDMTVI                    B
 98 STGVFTTKETASAHL KGGAKRVI I SAPSKDAPMFVVGVNL EKFNPSEKVI                    C
 96 STGVFTMEKACAHL KGGAKRVI I SAPSADAPMFVMGVNHEKYDKSLKI V                     D
 96 STGVFTI TEKASLHL KGGAKRVI SAPSADAPMFVVGVNHEKYENSLKVV

A
101 SNASCTTNCLAPLAKVI EGLMTTVHSI TATQKTVDGPSHKDWR                             B
148 SNASCTTNCLAPLAKVVNDKYGI EEGLMTTVHAI TATQKTVDGPSKKDWR                      C
146 SNASCTTNCLAPLAKVI NDTFGI VEGLMTTVHAI TATQKTVDGPSGKLWR                     D
146 SNASCTTNCLAPLAKVI NDNFGI VEGLMTTVHAFTATQKTVDGPSGKLWR

A
151 GGRTASGNI I PSSTGAAKA                                                     B
198 GGRGASANI I PSSTGAAKA                                                     C
196 DGRGAAQNI I PASTGAAKA                                                     D
196 DGRGACQNI I PASTGAAKA

A: Yarrowia lipolytica    (SEQ ID NO:12)
B: Schizosaccharomyces pombe    (amino acids 48-216 of SEQ ID NO:2)
C: Gallus gallus    (amino acids 46-214 of SEQ ID NO:6)
D: Xenopus laevis    (amino acids 46-214 of SEQ ID NO:5)
```

```
  1 MPKLVLVRHGQSEWNEKNLFTGWDVKLSAKGQQEAARACELLKEKKVYE       A
  1 MPKILIIIRHGQSDWNEKNLFTGWDVKLSFLGHTEAKRAGTLLKESCLKF       B

51 DVLYTSKLSRAIQTANIALEKADRLWIPVNRSWRLNERHYCDLQGKDKAE       A
 51 QILYTSELSRAIQTANIALDEADRLWIFTKRSWRLNERHYGALQGKDKAA       B

101 TLKKFGEEKFNTYRRSFDVPPPIDASSPSQKGDERYKYVLPNVLPETF         A
101 TLAEYCPEQFQLWRRSFDVPPPPIADDKWSQYNDERYQDIPKIILFKTE        B

151 SLALVIDRLLPYWQDVIAKDLISGKTVMIAAHGNSLRGLVKHIEGISDAF       A
151 SIKLVIDRLLPYYNSDIVPDIKAGKTVLIAAHGNSLRALVKHLDGISIDD       B

201 IAKLNIPTGIPLVFELDENLKPSKPSYYLDPEAAAGAAAAVANQGKR          A
201 IAALNIPTGIPLVIRP.                                       B
```

A: *Saccharomyces cerevisiae* (SEQ ID NO:13; GenBank Accession No. NP_012770)
B: *Yarrowia lipolytica* (SEQ ID NO:16)

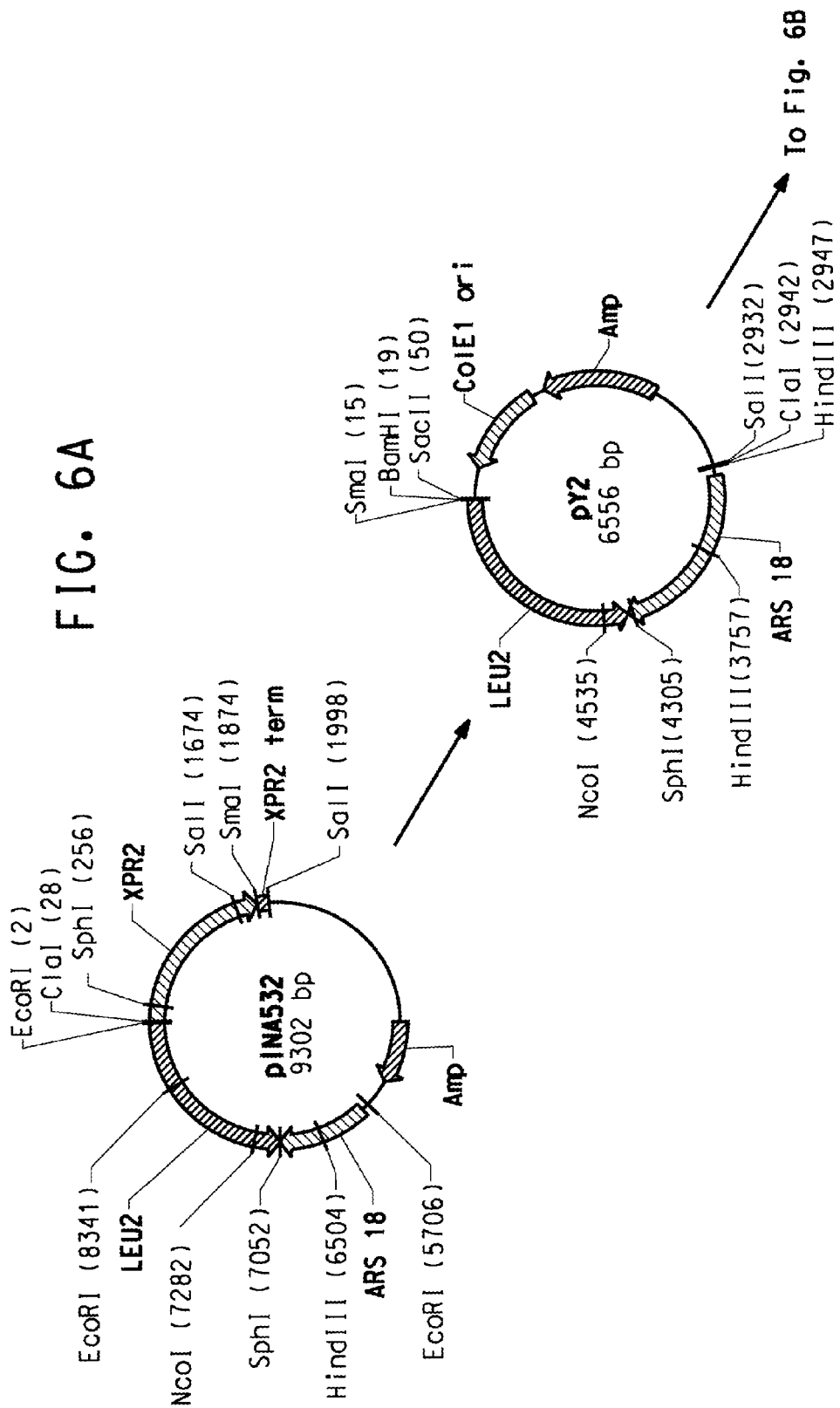

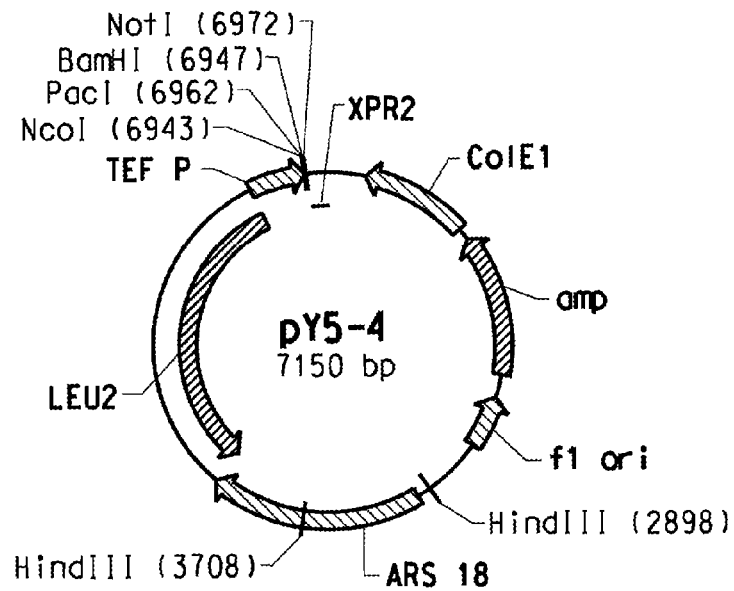
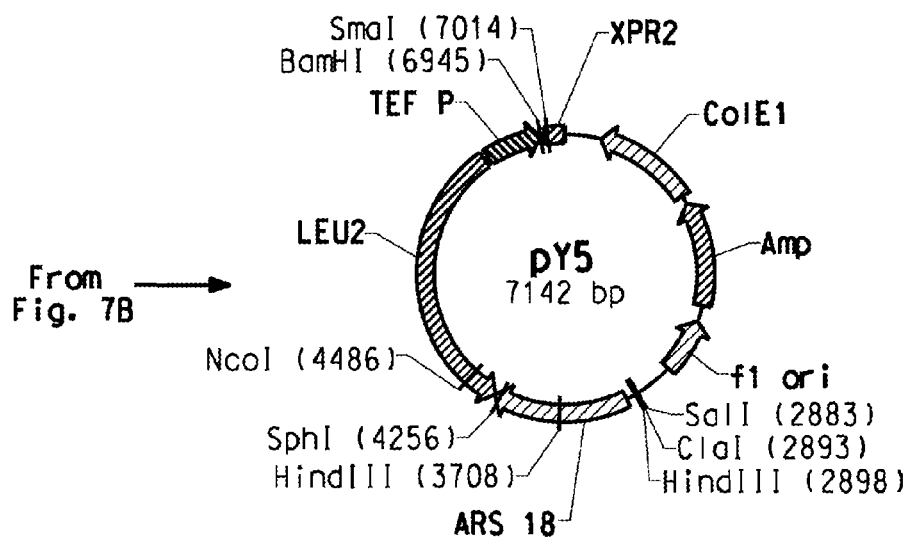
From
Fig. 7B →
FIG. 6C

SEQUENCE LISTING

<160> NUMBER OF SEQ ID NOS: 60

<210> SEQ ID NO 1
<211> LENGTH: 332
<212> TYPE: PRT
<213> ORGANISM: Sacchromyces cerevisiae (Genbank Accession No. CAA24607)

<400> SEQUENCE: 1

```
Met Val Arg Val Ala Ile Asn Gly Phe Gly Arg Ile Gly Arg Leu Val
1               5                   10                  15

Met Arg Ile Ala Leu Ser Arg Pro Asn Val Glu Val Val Ala Leu Asn
            20                  25                  30

Asp Pro Phe Ile Thr Asn Asp Tyr Ala Ala Tyr Met Phe Lys Tyr Asp
        35                  40                  45

Ser Thr His Gly Arg Tyr Ala Gly Glu Val Ser His Asp Asp Lys His
    50                  55                  60

Ile Ile Val Asp Gly Lys Lys Ile Ala Thr Tyr Gln Glu Arg Asp Pro
65                  70                  75                  80

Ala Asn Leu Pro Trp Gly Ser Ser Asn Val Asp Ile Ala Ile Asp Ser
```

```
                    85                  90                  95
Thr Gly Val Phe Lys Glu Leu Asp Thr Ala Gln Lys His Ile Asp Ala
            100                 105                 110
Gly Ala Lys Lys Val Val Ile Thr Ala Pro Ser Ser Thr Ala Pro Met
        115                 120                 125
Phe Val Met Gly Val Asn Glu Val Lys Tyr Thr Ser Asp Leu Lys Ile
    130                 135                 140
Val Ser Asn Ala Ser Cys Thr Thr Asn Cys Leu Ala Pro Leu Ala Lys
145                 150                 155                 160
Val Ile Asn Asp Ala Phe Gly Ile Glu Glu Gly Leu Met Thr Thr Val
                165                 170                 175
His Ser Leu Thr Ala Thr Gln Lys Thr Val Asp Gly Pro Ser His Lys
            180                 185                 190
Asp Trp Arg Gly Gly Arg Thr Ala Ser Gly Asn Ile Ile Pro Ser Ser
        195                 200                 205
Thr Gly Ala Ala Lys Ala Val Gly Lys Val Leu Pro Glu Leu Gln Gly
    210                 215                 220
Lys Leu Thr Gly Met Ala Phe Arg Val Pro Thr Val Asp Val Ser Val
225                 230                 235                 240
Val Asp Leu Thr Val Lys Leu Asp Lys Glu Thr Thr Tyr Asp Glu Ile
                245                 250                 255
Lys Lys Val Val Lys Ala Ala Ala Glu Gly Lys Leu Lys Gly Val Leu
            260                 265                 270
Gly Tyr Thr Glu Asp Ala Val Val Ser Ser Asp Phe Leu Gly Asp Ser
        275                 280                 285
His Ser Ser Ile Phe Asp Ala Ser Ala Gly Ile Gln Leu Ser Pro Lys
    290                 295                 300
Phe Val Lys Leu Val Ser Trp Tyr Asp Asn Glu Tyr Gly Tyr Ser Thr
305                 310                 315                 320
Arg Val Val Asp Leu Val Glu His Ile Ala Lys Ala
                325                 330

<210> SEQ ID NO 2
<211> LENGTH: 335
<212> TYPE: PRT
<213> ORGANISM: Schizosaccharomyces pombe (Genbank Accession No.
      NP_595236)

<400> SEQUENCE: 2

Met Ala Ile Pro Lys Val Gly Ile Asn Gly Phe Gly Arg Ile Gly Arg
1               5                   10                  15
Ile Val Leu Arg Asn Ala Ile Leu Thr Gly Lys Ile Gln Val Val Ala
            20                  25                  30
Val Asn Asp Pro Phe Ile Asp Leu Asp Tyr Met Ala Tyr Met Phe Lys
        35                  40                  45
Tyr Asp Ser Thr His Gly Arg Phe Glu Gly Ser Val Glu Thr Lys Gly
    50                  55                  60
Gly Lys Leu Val Ile Asp Gly His Ser Ile Asp Val His Asn Glu Arg
65                  70                  75                  80
Asp Pro Ala Asn Ile Lys Trp Ser Ala Ser Gly Ala Glu Tyr Val Ile
                85                  90                  95
Glu Ser Thr Gly Val Phe Thr Thr Lys Glu Thr Ala Ser Ala His Leu
            100                 105                 110
Lys Gly Gly Ala Lys Arg Val Ile Ile Ser Ala Pro Ser Lys Asp Ala
        115                 120                 125
```

-continued

Pro Met Phe Val Val Gly Val Asn Leu Glu Lys Phe Asn Pro Ser Glu
    130                 135                 140

Lys Val Ile Ser Asn Ala Ser Cys Thr Thr Asn Cys Leu Ala Pro Leu
145                 150                 155                 160

Ala Lys Val Ile Asn Asp Thr Phe Gly Ile Glu Gly Leu Met Thr
                165                 170                 175

Thr Val His Ala Thr Thr Ala Thr Gln Lys Thr Val Asp Gly Pro Ser
            180                 185                 190

Lys Lys Asp Trp Arg Gly Gly Arg Gly Ala Ser Ala Asn Ile Ile Pro
            195                 200                 205

Ser Ser Thr Gly Ala Ala Lys Ala Val Gly Lys Val Ile Pro Ala Leu
    210                 215                 220

Asn Gly Lys Leu Thr Gly Met Ala Phe Arg Val Pro Thr Pro Asp Val
225                 230                 235                 240

Ser Val Val Asp Leu Thr Val Lys Leu Ala Lys Pro Thr Asn Tyr Glu
                245                 250                 255

Asp Ile Lys Ala Ala Ile Lys Ala Ala Ser Glu Gly Pro Met Lys Gly
            260                 265                 270

Val Leu Gly Tyr Thr Glu Asp Ser Val Val Ser Thr Asp Phe Cys Gly
            275                 280                 285

Asp Asn His Ser Ser Ile Phe Asp Ala Ser Ala Gly Ile Gln Leu Ser
    290                 295                 300

Pro Gln Phe Val Lys Leu Val Ser Trp Tyr Asp Asn Glu Trp Gly Tyr
305                 310                 315                 320

Ser His Arg Val Val Asp Leu Val Ala Tyr Thr Ala Ser Lys Asp
                325                 330                 335

<210> SEQ ID NO 3
<211> LENGTH: 338
<212> TYPE: PRT
<213> ORGANISM: Aspergillus oryzae (Genbank Accession No. AAK08065)

<400> SEQUENCE: 3

Met Ala Thr Pro Lys Val Gly Ile Asn Gly Phe Gly Arg Ile Gly Arg
1               5                   10                  15

Ile Val Phe Arg Asn Ala Ile Ala Ser Gly Asp Val Asp Val Val Ala
                20                  25                  30

Val Asn Asp Pro Phe Ile Glu Thr His Tyr Ala Ala Tyr Met Leu Lys
            35                  40                  45

Tyr Asp Ser Thr His Gly Arg Phe Gln Gly Thr Ile Glu Thr Tyr Asp
    50                  55                  60

Glu Gly Leu Ile Val Asn Gly Lys Lys Ile Arg Phe Phe Ala Glu Arg
65                  70                  75                  80

Asp Pro Ala Ala Ile Pro Trp Gly Ser Ala Gly Ala Ala Tyr Ile Val
                85                  90                  95

Glu Ser Thr Gly Val Phe Thr Thr Glu Lys Ala Ser Ala His Leu
            100                 105                 110

Lys Gly Gly Ala Lys Lys Val Ile Ile Ser Ala Pro Ser Ala Asp Ala
        115                 120                 125

Pro Met Phe Val Met Gly Val Asn Asn Lys Glu Tyr Lys Thr Asp Ile
    130                 135                 140

Asn Val Leu Ser Asn Ala Ser Cys Thr Thr Asn Cys Leu Ala Pro Leu
145                 150                 155                 160

Ala Lys Val Ile Asn Asp Asn Phe Gly Leu Val Glu Gly Leu Met Thr

```
                            165                 170                 175
Thr Val His Ser Tyr Thr Ala Thr Gln Lys Thr Val Asp Ala Pro Ser
                180                 185                 190
Ala Lys Asp Trp Arg Gly Gly Arg Thr Ala Ala Gln Asn Ile Ile Pro
            195                 200                 205
Ser Ser Thr Gly Ala Ala Lys Ala Val Gly Lys Val Ile Pro Ser Leu
        210                 215                 220
Asn Gly Lys Leu Thr Gly Met Ser Met Arg Val Pro Thr Ala Asn Val
225                 230                 235                 240
Ser Val Val Asp Leu Thr Cys Arg Thr Glu Lys Ala Val Thr Tyr Glu
                245                 250                 255
Asp Ile Lys Lys Thr Ile Lys Ala Ala Ser Glu Glu Gly Glu Leu Lys
                260                 265                 270
Gly Ile Leu Gly Tyr Thr Glu Asp Asp Ile Val Ser Thr Asp Leu Ile
            275                 280                 285
Gly Asp Ala His Ser Ser Ile Phe Asp Ala Lys Ala Gly Ile Ala Leu
        290                 295                 300
Asn Glu His Phe Ile Lys Leu Val Ser Trp Tyr Asp Asn Glu Trp Gly
305                 310                 315                 320
Tyr Ser Arg Arg Val Val Asp Leu Ile Ala Tyr Ile Ser Lys Val Asp
                325                 330                 335
Gly Gln

<210> SEQ ID NO 4
<211> LENGTH: 333
<212> TYPE: PRT
<213> ORGANISM: Paralichthys olivaceus (Genbank Accession No. BAA88638)

<400> SEQUENCE: 4

Met Val Lys Val Gly Ile Asn Gly Phe Gly Arg Ile Gly Arg Leu Val
1               5                   10                  15
Thr Arg Ala Ala Phe Thr Ser Lys Lys Val Glu Ile Val Ala Ile Asn
                20                  25                  30
Asp Pro Phe Ile Asp Leu Glu Tyr Met Val Tyr Met Phe Lys Tyr Asp
            35                  40                  45
Ser Thr His Gly Arg Phe Lys Gly Glu Val Lys Ile Glu Gly Asp Lys
        50                  55                  60
Leu Val Ile Asp Gly His Lys Ile Thr Val Phe His Glu Arg Asp Pro
65                  70                  75                  80
Thr Asn Ile Lys Trp Gly Asp Ala Gly Ala His Tyr Val Val Glu Ser
                85                  90                  95
Thr Gly Val Phe Thr Thr Ile Glu Lys Ala Ser Ala His Leu Lys Gly
            100                 105                 110
Gly Ala Lys Lys Val Ile Ile Ser Ala Pro Ser Ala Asp Ala Pro Met
        115                 120                 125
Phe Val Met Gly Val Asn His Glu Lys Tyr Asp Lys Ser Leu Gln Val
    130                 135                 140
Val Ser Asn Ala Ser Cys Thr Thr Asn Cys Leu Ala Pro Leu Ala Lys
145                 150                 155                 160
Val Ile Asn Asp Asn Phe Gly Ile Ile Glu Gly Leu Met Ser Thr Val
                165                 170                 175
His Ala Ile Thr Ala Thr Gln Lys Thr Val Asp Gly Pro Ser Gly Lys
            180                 185                 190
Leu Trp Arg Asp Gly Arg Gly Ala Ser Gln Asn Ile Ile Pro Ala Ser
```

```
              195                 200                 205
Thr Gly Ala Ala Lys Ala Val Gly Lys Val Ile Pro Glu Leu Asn Gly
    210                 215                 220

Lys Leu Thr Gly Met Ala Phe Arg Val Pro Thr Pro Asn Val Ser Val
225                 230                 235                 240

Val Asp Leu Thr Val Arg Leu Glu Lys Pro Ala Ser Tyr Glu Asn Ile
                245                 250                 255

Lys Lys Val Val Lys Ala Ala Glu Gly Pro Met Lys Gly Tyr Leu
                260                 265                 270

Ala Tyr Thr Glu His Gln Val Val Ser Thr Asp Phe Asn Gly Asp Thr
                275                 280                 285

His Ser Ser Ile Phe Asp Ala Gly Ala Gly Ile Ala Leu Asn Asp His
                290                 295                 300

Phe Val Lys Leu Val Ser Trp Tyr Asp Asn Glu Phe Ala Tyr Ser Asn
305                 310                 315                 320

Arg Val Cys Asp Leu Met Ala His Met Ala Ser Lys Glu
                325                 330

<210> SEQ ID NO 5
<211> LENGTH: 333
<212> TYPE: PRT
<213> ORGANISM: Xenopus laevis (Genbank Accession No. P51469)

<400> SEQUENCE: 5

Met Val Lys Val Gly Ile Asn Gly Phe Gly Cys Ile Gly Arg Leu Val
1               5                   10                  15

Thr Arg Ala Ala Phe Asp Ser Gly Lys Val Gln Val Val Ala Ile Asn
                20                  25                  30

Asp Pro Phe Ile Asp Leu Asp Tyr Met Val Tyr Met Phe Lys Tyr Asp
                35                  40                  45

Ser Thr His Gly Arg Phe Lys Gly Thr Val Lys Ala Glu Asn Gly Lys
            50                  55                  60

Leu Ile Ile Asn Asp Gln Val Ile Thr Val Phe Gln Glu Arg Asp Pro
65                  70                  75                  80

Ser Ser Ile Lys Trp Gly Asp Ala Gly Ala Val Tyr Val Val Glu Ser
                85                  90                  95

Thr Gly Val Phe Thr Thr Thr Glu Lys Ala Ser Leu His Leu Lys Gly
                100                 105                 110

Gly Ala Lys Arg Val Val Ile Ser Ala Pro Ser Ala Asp Ala Pro Met
            115                 120                 125

Phe Val Val Gly Val Asn His Glu Lys Tyr Glu Asn Ser Leu Lys Val
        130                 135                 140

Val Ser Asn Ala Ser Cys Thr Thr Asn Cys Leu Ala Pro Leu Ala Lys
145                 150                 155                 160

Val Ile Asn Asp Asn Phe Gly Ile Val Glu Gly Leu Met Thr Thr Val
                165                 170                 175

His Ala Phe Thr Ala Thr Gln Lys Thr Val Asp Gly Pro Ser Gly Lys
            180                 185                 190

Leu Trp Arg Asp Gly Arg Gly Ala Gly Gln Asn Ile Ile Pro Ala Ser
        195                 200                 205

Thr Gly Ala Ala Lys Ala Val Gly Lys Val Ile Pro Glu Leu Asn Gly
    210                 215                 220

Lys Ile Thr Gly Met Ala Phe Arg Val Pro Thr Pro Asn Val Ser Val
225                 230                 235                 240
```

-continued

```
Val Asp Leu Thr Cys Arg Leu Gln Lys Pro Ala Lys Tyr Asp Asp Ile
            245                 250                 255

Lys Ala Ala Ile Lys Thr Ala Ser Glu Gly Pro Met Lys Gly Ile Leu
        260                 265                 270

Gly Tyr Thr Gln Asp Gln Val Val Ser Thr Asp Phe Asn Gly Asp Thr
            275                 280                 285

His Ser Ser Ile Phe Asp Ala Asp Ala Gly Ile Ala Leu Asn Glu Asn
    290                 295                 300

Phe Val Lys Leu Val Ser Trp Tyr Asp Asn Glu Cys Gly Tyr Ser Asn
305                 310                 315                 320

Arg Val Val Asp Leu Val Cys His Met Ala Ser Lys Glu
                325                 330
```

<210> SEQ ID NO 6
<211> LENGTH: 333
<212> TYPE: PRT
<213> ORGANISM: Gallus gallus (Genbank Accession No. DECHG3)

<400> SEQUENCE: 6

```
Met Val Lys Val Gly Val Asn Gly Phe Gly Arg Ile Gly Arg Leu Val
1               5                   10                  15

Thr Arg Ala Ala Val Leu Ser Gly Lys Val Gln Val Val Ala Ile Asn
            20                  25                  30

Asp Pro Phe Ile Asp Leu Asn Tyr Met Val Tyr Met Phe Lys Tyr Asp
        35                  40                  45

Ser Thr His Gly His Phe Lys Gly Thr Val Lys Ala Glu Asn Gly Lys
    50                  55                  60

Leu Val Ile Asn Gly His Ala Ile Thr Ile Phe Gln Glu Arg Asp Pro
65                  70                  75                  80

Ser Asn Ile Lys Trp Ala Asp Ala Gly Ala Glu Tyr Val Val Glu Ser
                85                  90                  95

Thr Gly Val Phe Thr Thr Met Glu Lys Ala Gly Ala His Leu Lys Gly
            100                 105                 110

Gly Ala Lys Arg Val Ile Ile Ser Ala Pro Ser Ala Asp Ala Pro Met
        115                 120                 125

Phe Val Met Gly Val Asn His Glu Lys Tyr Asp Lys Ser Leu Lys Ile
    130                 135                 140

Val Ser Asn Ala Ser Cys Thr Thr Asn Cys Leu Ala Pro Leu Ala Lys
145                 150                 155                 160

Val Ile His Asp Asn Phe Gly Ile Val Glu Gly Leu Met Thr Thr Val
                165                 170                 175

His Ala Ile Thr Ala Thr Gln Lys Thr Val Asp Gly Pro Ser Gly Lys
            180                 185                 190

Leu Trp Arg Asp Gly Arg Gly Ala Ala Gln Asn Ile Ile Pro Ala Ser
        195                 200                 205

Thr Gly Ala Ala Lys Ala Val Gly Lys Val Ile Pro Glu Leu Asn Gly
    210                 215                 220

Lys Leu Thr Gly Met Ala Phe Arg Val Pro Thr Pro Asn Val Ser Val
225                 230                 235                 240

Val Asp Leu Thr Cys Arg Leu Glu Lys Pro Ala Lys Tyr Asp Asp Ile
                245                 250                 255

Lys Arg Val Val Lys Ala Ala Ala Asp Gly Pro Leu Lys Gly Ile Leu
            260                 265                 270

Gly Tyr Thr Glu Asp Gln Val Val Ser Cys Asp Phe Asn Gly Asp Ser
        275                 280                 285
```

```
His Ser Ser Thr Phe Asp Ala Gly Ala Gly Ile Ala Leu Asn Asp His
    290                 295                 300

Phe Val Lys Leu Val Ser Trp Tyr Asp Asn Glu Phe Gly Tyr Ser Asn
305                 310                 315                 320

Arg Val Val Asp Leu Met Val His Met Ala Ser Lys Glu
                325                 330

<210> SEQ ID NO 7
<211> LENGTH: 7
<212> TYPE: PRT
<213> ORGANISM: Artificial Sequence
<220> FEATURE:
<223> OTHER INFORMATION: Conserved protein motif in GPD

<400> SEQUENCE: 7

Lys Tyr Asp Ser Thr His Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Conserved protein motif in GPD

<400> SEQUENCE: 8

Thr Gly Ala Ala Lys Ala Val
1               5

<210> SEQ ID NO 9
<211> LENGTH: 20
<212> TYPE: DNA
<213> ORGANISM: Artificial Sequence
<220> FEATURE:
<223> OTHER INFORMATION: Degenerate primer YL193

<400> SEQUENCE: 9
aagtacgayt cbacycaygg                                              20

<210> SEQ ID NO 10
<211> LENGTH: 20
<212> TYPE: DNA
<213> ORGANISM: Artificial Sequence
<220> FEATURE:
<223> OTHER INFORMATION: Degenerate primer YL194

<400> SEQUENCE: 10
acrgccttrg crgcdccrgt                                              20

<210> SEQ ID NO 11
<211> LENGTH: 507
<212> TYPE: DNA
<213> ORGANISM: Yarrowia lipolytica

<400> SEQUENCE: 11
aagtacgact ccacccacgg ccgattcaag ggcaaggtcg aggccaagga cggcggtctg    60
atcatcgacg gcaagcacat ccaggtcttc ggtgagcgag acccctccaa catcccctgg   120
ggtaaggccg gtgccgacta cgttgtcgag tccaccggtg tcttcaccgg caaggaggct   180
gcctccgccc acctcaaggg tggtgccaag aaggtcatca tctccgcccc ctccggtgac   240
gcccccatgt tcgttgtcgg tgtcaacctc gacgcctaca gcccgacat gaccgtcatc   300 tccaacgctt cttgtaccac caactgtctg gctccccttg ccaaggttgt caacgacaag   360
```

```
tacggaatca ttgagggtct catgaccacc gtccactcca tcaccgccac ccagaagacc    420
gttgacggtc cttcccacaa ggactggcga ggtggccgaa ccgcctctgg taacatcatc    480
ccctcttcca ccggagccgc caaggct                                        507
```

<210> SEQ ID NO 12
<211> LENGTH: 169
<212> TYPE: PRT
<213> ORGANISM: Yarrowia lipolytica

<400> SEQUENCE: 12

```
Lys Tyr Asp Ser Thr His Gly Arg Phe Lys Gly Lys Val Glu Ala Lys
1               5                   10                  15

Asp Gly Gly Leu Ile Ile Asp Gly Lys His Ile Gln Val Phe Gly Glu
            20                  25                  30

Arg Asp Pro Ser Asn Ile Pro Trp Gly Lys Ala Gly Ala Asp Tyr Val
        35                  40                  45

Val Glu Ser Thr Gly Val Phe Thr Gly Lys Glu Ala Ala Ser Ala His
    50                  55                  60

Leu Lys Gly Gly Ala Lys Lys Val Ile Ile Ser Ala Pro Ser Gly Asp
65                  70                  75                  80

Ala Pro Met Phe Val Val Gly Val Asn Leu Asp Ala Tyr Lys Pro Asp
                85                  90                  95

Met Thr Val Ile Ser Asn Ala Ser Cys Thr Thr Asn Cys Leu Ala Pro
            100                 105                 110

Leu Ala Lys Val Val Asn Asp Lys Tyr Gly Ile Ile Glu Gly Leu Met
        115                 120                 125

Thr Thr Val His Ser Ile Thr Ala Thr Gln Lys Thr Val Asp Gly Pro
    130                 135                 140

Ser His Lys Asp Trp Arg Gly Gly Arg Thr Ala Ser Gly Asn Ile Ile
145                 150                 155                 160

Pro Ser Ser Thr Gly Ala Ala Lys Ala
                165
```

<210> SEQ ID NO 13
<211> LENGTH: 245
<212> TYPE: PRT
<213> ORGANISM: Saccharomyces cerevisiae (GenBank Accesssion No.
    NP_012770)

<400> SEQUENCE: 13

```
Met Pro Lys Leu Val Leu Val Arg His Gly Gln Ser Glu Trp Asn Glu
1               5                   10                  15

Lys Asn Leu Phe Thr Gly Trp Val Asp Val Lys Leu Ser Ala Lys Gly
            20                  25                  30

Gln Gln Glu Ala Ala Arg Ala Gly Glu Leu Leu Lys Glu Lys Lys Val
        35                  40                  45

Tyr Pro Asp Val Leu Tyr Thr Ser Lys Leu Ser Arg Ala Ile Gln Thr
    50                  55                  60

Ala Asn Ile Ala Leu Glu Lys Ala Asp Arg Leu Trp Ile Pro Val Asn
65                  70                  75                  80

Arg Ser Trp Arg Leu Asn Glu Arg His Tyr Gly Asp Leu Gln Gly Lys
                85                  90                  95

Asp Lys Ala Glu Thr Leu Lys Lys Phe Gly Glu Glu Lys Phe Asn Thr
            100                 105                 110

Tyr Arg Arg Ser Phe Asp Val Pro Pro Pro Pro Ile Asp Ala Ser Ser
```

```
            115                 120                 125
Pro Phe Ser Gln Lys Gly Asp Glu Arg Tyr Lys Tyr Val Asp Pro Asn
    130                 135                 140

Val Leu Pro Glu Thr Glu Ser Leu Ala Leu Val Ile Asp Arg Leu Leu
145                 150                 155                 160

Pro Tyr Trp Gln Asp Val Ile Ala Lys Asp Leu Leu Ser Gly Lys Thr
                165                 170                 175

Val Met Ile Ala Ala His Gly Asn Ser Leu Arg Gly Leu Val Lys His
                180                 185                 190

Leu Glu Gly Ile Ser Asp Ala Asp Ile Ala Lys Leu Asn Ile Pro Thr
                195                 200                 205

Gly Ile Pro Leu Val Phe Glu Leu Asp Glu Asn Leu Lys Pro Ser Lys
    210                 215                 220

Pro Ser Tyr Tyr Leu Asp Pro Glu Ala Ala Ala Gly Ala Ala Ala
225                 230                 235                 240

Val Ala Asn Gln Gly
            245

<210> SEQ ID NO 14
<211> LENGTH: 1049
<212> TYPE: DNA
<213> ORGANISM: Yarrowia lipolytica
<220> FEATURE:
<221> NAME/KEY: misc_feature
<222> LOCATION: (1020)..(1020)
<223> OTHER INFORMATION: n is a, c, g, or t

<400> SEQUENCE: 14
caattgagtg cgagcgacac aattgggtgt cacgtgccyt aattgacctc ggatcgtgga      60
gycccccagtt atacagcaac cacgaggtgc atgagtagga gacgtcmcca gacaataggg    120
ttttttttgga ctggagaggg tagggcaaaa gcgctcaacg ggctgtttgg ggagctatgg    180
gggaggaatt ggcgatattt gtgaggttga cggctccgat ttgcgtgttt tgtcgcttct    240
gcatctcccc atacccatat cttccctccc cacctctttc cacgataatt ttacggatca    300
gcaataaggt tccttctcct agtttccacg yccatatata tctatgctgc gtcgtccttt    360
tcgtgacatc accaaaacac atacaaaaat gcctaaactg attctgctgc gacacggcca    420
gtccgactgg aacgagaaga acctgttcac cggatgggtc gacgtcaagt ctccgagctc    480
ggccacaccg aggccaagcg agccggtact ctgctcaagg agtccggtct caagccccag    540
attctctaca cctccgagct ctctcgagcc atccagaccg ccaacattgc tctggatgag    600
gccgaccgac tgtggatccc caccaagcga tcgtggcgac tcaacgagcg acactacggc    660
gctctgcagg gcaaggacaa ggccgccact ctcgccgagt acggccccga gcagttccag    720
ctctggcgac gatcttttga cgtccctcct cccctatcg ctgacgacga caagtggtct    780
cagtacaacg acgagcgata ccaggacatc cccaaggata ttctgcccaa gaccgagtct    840
ctgaagctcg tgattgaccg actccttcct tactacaact ccgacattgt ccccgacctt    900
aaggccggca agaccgtcct cattgctgcc cacgaaact ccctccgagc tctcgtcaag    960
cacctcgacg gtatctccga tgacgatatc gccgccctta acatcccac cggtatcccn  1020
ctcgtgctac gaccttgatg acaacctca                                     1049

<210> SEQ ID NO 15
<211> LENGTH: 651
<212> TYPE: DNA
<213> ORGANISM: Yarrowia lipolytica
```

```
<220> FEATURE:
<221> NAME/KEY: misc_feature
<222> LOCATION: (633)..(633)
<223> OTHER INFORMATION: n is a, c, g, or t

<400> SEQUENCE: 15
atgcctaaac tgattctgct gcgacacggc cagtccgact ggaacgagaa gaacctgttc    60
accggatggg tcgacgtcaa gctctccgag ctcggccaca ccgaggccaa gcgagccggt   120
actctgctca aggagtccgg tctcaagccc cagattctct acacctccga gctctctcga   180
gccatccaga ccgccaacat tgctctggat gaggccgacc gactgtggat ccccaccaag   240
cgatcgtggc gactcaacga gcgacactac ggcgctctgc agggcaagga caaggccgcc   300
actctcgccg agtacggccc cgagcagttc cagctctggc gacgatcttt tgacgtccct   360
cctcccccta tcgctgacga cgacaagtgg tctcagtaca acgacgagcg ataccaggac   420
atccccaagg atattctgcc caagaccgag tctctgaagc tcgtgattga ccgactcctt   480
ccttactaca actccgacat tgtccccgac cttaaggccg gcaagaccgt cctcattgct   540
gcccacggaa actccctccg agctctcgtc aagcacctcg acggtatctc cgatgacgat   600
atcgccgccc ttaacatccc caccggtatc ccnctcgtgc tacgaccttg a            651

<210> SEQ ID NO 16
<211> LENGTH: 216
<212> TYPE: PRT
<213> ORGANISM: Yarrowia lipolytica

<400> SEQUENCE: 16

Met Pro Lys Leu Ile Leu Leu Arg His Gly Gln Ser Asp Trp Asn Glu
1               5                   10                  15

Lys Asn Leu Phe Thr Gly Trp Val Asp Val Lys Leu Ser Glu Leu Gly
            20                  25                  30

His Thr Glu Ala Lys Arg Ala Gly Thr Leu Leu Lys Glu Ser Gly Leu
        35                  40                  45

Lys Pro Gln Ile Leu Tyr Thr Ser Glu Leu Ser Arg Ala Ile Gln Thr
    50                  55                  60

Ala Asn Ile Ala Leu Asp Glu Ala Asp Arg Leu Trp Ile Pro Thr Lys
65                  70                  75                  80

Arg Ser Trp Arg Leu Asn Glu Arg His Tyr Gly Ala Leu Gln Gly Lys
                85                  90                  95

Asp Lys Ala Ala Thr Leu Ala Glu Tyr Gly Pro Glu Gln Phe Gln Leu
            100                 105                 110

Trp Arg Arg Ser Phe Asp Val Pro Pro Pro Ile Ala Asp Asp Asp
        115                 120                 125

Lys Trp Ser Gln Tyr Asn Asp Glu Arg Tyr Gln Asp Ile Pro Lys Asp
    130                 135                 140

Ile Leu Pro Lys Thr Glu Ser Leu Lys Leu Val Ile Asp Arg Leu Leu
145                 150                 155                 160

Pro Tyr Tyr Asn Ser Asp Ile Val Pro Asp Leu Lys Ala Gly Lys Thr
                165                 170                 175

Val Leu Ile Ala Ala His Gly Asn Ser Leu Arg Ala Leu Val Lys His
            180                 185                 190

Leu Asp Gly Ile Ser Asp Asp Ile Ala Ala Leu Asn Ile Pro Thr
        195                 200                 205

Gly Ile Pro Leu Val Leu Arg Pro
    210                 215
```

<210> SEQ ID NO 17
<211> LENGTH: 26
<212> TYPE: DNA
<213> ORGANISM: Artificial Sequence
<220> FEATURE:
<223> OTHER INFORMATION: Primer YL206

<400> SEQUENCE: 17
ccttgccggt gaagacaccg gtggac                                              26

<210> SEQ ID NO 18
<211> LENGTH: 25
<212> TYPE: DNA
<213> ORGANISM: Artificial Sequence
<220> FEATURE:
<223> OTHER INFORMATION: Primer YL196

<400> SEQUENCE: 18
gacgtcgacc catccggtga acagg                                               25

<210> SEQ ID NO 19
<211> LENGTH: 28
<212> TYPE: DNA
<213> ORGANISM: Artificial Sequence
<220> FEATURE:
<223> OTHER INFORMATION: Primer YL207

<400> SEQUENCE: 19
gaagacctgg atgtgcttgc cgtcgatg                                            28

<210> SEQ ID NO 20
<211> LENGTH: 23
<212> TYPE: DNA
<213> ORGANISM: Artificial Sequence
<220> FEATURE:
<223> OTHER INFORMATION: Primer YL197

<400> SEQUENCE: 20
gagcagagta ccggctcgct tgg                                                 23

<210> SEQ ID NO 21
<211> LENGTH: 24
<212> TYPE: DNA
<213> ORGANISM: Artificial Sequence
<220> FEATURE:
<223> OTHER INFORMATION: Primer YL208

<400> SEQUENCE: 21
gaccttgccc ttgaatcggc cgtg                                                24

<210> SEQ ID NO 22
<211> LENGTH: 25
<212> TYPE: DNA
<213> ORGANISM: Artificial Sequence
<220> FEATURE:
<223> OTHER INFORMATION: Primer YL198

<400> SEQUENCE: 22
gaatctgggg cttgagaccg gactc                                               25

<210> SEQ ID NO 23
<211> LENGTH: 1848
<212> TYPE: DNA
<213> ORGANISM: Yarrowia lipolytica

<400> SEQUENCE: 23

-continued

| | |
|---|---|
| gtgattgcct ctgaatactt tcaacaagtt acacccttcg cggcgacgat ctacagcccg | 60 |
| atcacatgaa ctttggccga gggatgatgt aatcgagtat cgtggtagtt caatacgtac | 120 |
| atgtacgatg ggtgcctcaa ttgtgcgata ctactacaag tgcagcacgc tcgtgcccgt | 180 |
| accctacttt gtcggacgtc cctgctccct cgttcaacat ctcaagctca acaatcagtg | 240 |
| ttggacactg caacgctagc agccggtacg tggctttagc cccatgctcc atgctccatg | 300 |
| ctccatgctc tgggcctatg agctagccgt ttggcgcaca tagcatagtg acatgtcgat | 360 |
| caagtcaaag tcgaggtgtg aaaacgggc tgcgggtcgc caggggcctc acaagcgcct | 420 |
| ccaccgcaga cgcccacctc gttagcgtcc attgcgatcg tctcggtaca tttggttaca | 480 |
| ttttgcgaca ggttgaaatg aatcggccga cgctcggtag tcggaaagag ccgggaccgg | 540 |
| ccggcgagca taaaccggac gcagtaggat gtcctgcacg ggtctttttg tggggtgtgg | 600 |
| agaaaggggt gcttggagat ggaagccggt agaaccgggc tgcttgtgct ggagatgga | 660 |
| agccggtaga accgggctgc ttgggggat ttggggccgc tgggctccaa agagggtag | 720 |
| gcatttcgtt ggggttacgt aattgcggca tttggggtcct gcgcgcatgt cccattggtc | 780 |
| agaattagtc cggataggag acttatcagc caatcacagc gccggatcca cctgtaggtt | 840 |
| gggttgggtg ggagcacccc tccacagagt agagtcaaac agcagcagca acatgatagt | 900 |
| tgggggtgtg cgtgttaaag gaaaaaaag aagcttgggt tatattcccg ctctatttag | 960 |
| aggttgcggg atagacgccg acggagggca atggcgccat ggaaccttgc ggatatcgat | 1020 |
| acgccgcggc ggactgcgtc cgaaccagct ccagcagcgt ttttccggg ccattgagcc | 1080 |
| gactgcgacc ccgccaacgt gtcttggccc acgcactcat gtcatgttgg tgttgggagg | 1140 |
| ccacttttta agtagcacaa ggcacctagc tcgcagcaag gtgtccgaac caagaagcg | 1200 |
| gctgcagtgg tgcaaacggg gcggaaacgg cgggaaaaag ccacggggc acgaattgag | 1260 |
| gcacgccctc gaatttgaga cgagtcacgg ccccattcgc ccgcgcaatg gctcgccaac | 1320 |
| gcccggtctt ttgcaccaca tcaggttacc ccaagccaaa cctttgtgtt aaaaagctta | 1380 |
| acatattata ccgaacgtag gtttggggcgg gcttgctccg tctgtccaag gcaacattta | 1440 |
| tataagggtc tgcatcgccg gctcaattga atcttttttc ttcttctctt ctctatattc | 1500 |
| attcttgaat taaacacaca tcaacatggc catcaaagtc ggtattaacg gattcgggcg | 1560 |
| aatcggacga attgtgagta ccatagaagg tgatggaaac atgacccaac agaaacagat | 1620 |
| gacaagtgtc atcgacccac cagagcccaa ttgagctcat actaacagtc gacaacctgt | 1680 |
| cgaaccaatt gatgactccc cgacaatgta ctaacacagg tcctgcgaaa cgctctcaag | 1740 |
| aaccctgagg tcgaggtcgt cgctgtgaac gaccccttca tcgacaccga gtacgctgct | 1800 |
| tacatgttca agtacgactc cacccacggc cgattcaagg gcaaggtc | 1848 |

<210> SEQ ID NO 24
<211> LENGTH: 2316
<212> TYPE: DNA
<213> ORGANISM: Yarrowia lipolytica

<400> SEQUENCE: 24

| | |
|---|---|
| gtgattgcct ctgaatactt tcaacaagtt acacccttcg cggcgacgat ctacagcccg | 60 |
| atcacatgaa ctttggccga gggatgatgt aatcgagtat cgtggtagtt caatacgtac | 120 |
| atgtacgatg ggtgcctcaa ttgtgcgata ctactacaag tgcagcacgc tcgtgcccgt | 180 |
| accctacttt gtcggacgtc cctgctccct cgttcaacat ctcaagctca acaatcagtg | 240 |

-continued

```
ttggacactg caacgctagc agccggtacg tggctttagc cccatgctcc atgctccatg    300
ctccatgctc tgggcctatg agctagccgt ttggcgcaca tagcatagtg acatgtcgat    360
caagtcaaag tcgaggtgtg gaaaacgggc tgcgggtcgc caggggcctc acaagcgcct    420
ccaccgcaga cgcccacctc gttagcgtcc attgcgatcg tctcggtaca tttggttaca    480
ttttgcgaca ggttgaaatg aatcggccga cgctcggtag tcggaaagag ccgggaccgg    540
ccggcgagca taaaccggac gcagtaggat gtcctgcacg ggtcttttg tggggtgtgg     600 agaaagggt gcttggagat ggaagccggt agaaccgggc tgcttgtgct tggagatgga     660
agccggtaga accgggctgc ttgggggat ttggggccgc tgggctccaa agaggggtag     720
gcatttcgtt ggggttacgt aattgcggca tttgggtcct gcgcgcatgt cccattggtc    780
agaattagtc cggataggag acttatcagc caatcacagc gccggatcca cctgtaggtt    840
gggttgggtg ggagcacccc tccacagagt agagtcaaac agcagcagca acatgatagt    900
tgggggtgtg cgtgttaaag gaaaaaaag aagcttgggt tatattcccg ctctatttag     960
aggttgcggg atagacgccg acggagggca atggcgccat ggaaccttgc ggatatcgat    1020
acgccgcggc ggactgcgtc cgaaccagct ccagcagcgt ttttccgggg ccattgagcc    1080
gactgcgacc ccgccaacgt gtcttggccc acgcactcat gtcatgttgg tgttgggagg    1140 ccactttta agtagcacaa ggcacctagc tcgcagcaag gtgtccgaac caaagaagcg     1200
gctgcagtgg tgcaaacggg gcggaaacgg cgggaaaaag ccacgggggc acgaattgag    1260
gcacgccctc gaatttgaga cgagtcacgg ccccattcgc ccgcgcaatg gctcgccaac    1320
gcccggtctt ttgcaccaca tcaggttacc ccaagccaaa cctttgtgtt aaaaagctta    1380
acatattata ccgaacgtag gtttgggcgg gcttgctccg tctgtccaag gcaacattta    1440
tataagggtc tgcatcgccg gctcaattga atctttttc ttcttctctt ctctatattc     1500
attcttgaat taaacacaca tcaacatggc catcaaagtc ggtattaacg gattcgggcg    1560
aatcggacga attgtgagta ccatagaagg tgatggaaac atgacccaac agaaacagat    1620
gacaagtgtc atcgacccac cagagcccaa ttgagctcat actaacagtc gacaacctgt    1680
cgaaccaatt gatgactccc cgacaatgta ctaacacagg tcctgcgaaa cgctctcaag    1740
aaccctgagg tcgaggtcgt cgctgtgaac gaccccttca tcgacaccga gtacgctgct    1800
tacatgttca agtacgactc cacccacggc cgattcaagg gcaaggtcga ggccaaggac    1860
ggcggtctga tcatcgacgg caagcacatc caggtcttcg gtgagcgaga ccctccaac     1920 atcccctggg gtaaggccgg tgccgactac gttgtcgagt ccaccggtgt cttcaccggc    1980
aaggaggctg cctccgccca cctcaagggt ggtgccaaga aggtcatcat ctccgccccc    2040
tccggtgacg cccccatgtt cgttgtcggt gtcaacctcg acgcctacaa gcccgacatg    2100
accgtcatct ccaacgcttc ttgtaccacc aactgtctgg ctccccttgc caaggttgtc    2160
aacgacaagt acgaatcat tgagggtctc atgaccaccg tccactccat caccgccacc    2220
cagaagaccg ttgacggtcc ttcccacaag gactggcgag gtggccgaac cgcctctggt    2280
aacatcatcc cctcttccac cggagccgcc aaggct                              2316
```

<210> SEQ ID NO 25
<211> LENGTH: 645
<212> TYPE: DNA
<213> ORGANISM: Yarrowia lipolytica

<400> SEQUENCE: 25

```
atggccatca agtcggtat taacggattc gggcgaatcg gacgaattgt cctgcgaaac    60
```

```
gctctcaaga accctgaggt cgaggtcgtc gctgtgaacg acccccttcat cgacaccgag    120 tacgctgctt acatgttcaa gtacgactcc acccacggcc gattcaaggg caaggtcgag    180
gccaaggacg gcggtctgat catcgacggc aagcacatcc aggtcttcgg tgagcgagac    240
ccctccaaca tccctggggg taaggccggt gccgactacg ttgtcgagtc caccggtgtc    300
ttcaccggca aggaggctgc ctccgcccac ctcaagggtg gtgccaagaa ggtcatcatc    360
tccgccccct ccggtgacgc ccccatgttc gttgtcggtg tcaacctcga cgcctacaag    420
cccgacatga ccgtcatctc caacgcttct tgtaccacca actgtctggc tccccttgcc    480
aaggttgtca acgacaagta cggaatcatt gagggtctca tgaccaccgt ccactccatc    540
accgccaccc agaagaccgt tgacggtcct cccacaagg actggcgagg tggccgaacc    600
gcctctggta acatcatccc ctcttccacc ggagccgcca aggct                    645
```

<210> SEQ ID NO 26
<211> LENGTH: 215
<212> TYPE: PRT
<213> ORGANISM: Yarrowia lipolytica

<400> SEQUENCE: 26

```
Met Ala Ile Lys Val Gly Ile Asn Gly Phe Gly Arg Ile Gly Arg Ile
1               5                   10                  15

Val Leu Arg Asn Ala Leu Lys Asn Pro Glu Val Glu Val Val Ala Val
            20                  25                  30

Asn Asp Pro Phe Ile Asp Thr Glu Tyr Ala Ala Tyr Met Phe Lys Tyr
        35                  40                  45

Asp Ser Thr His Gly Arg Phe Lys Gly Lys Val Glu Ala Lys Asp Gly
    50                  55                  60

Gly Leu Ile Ile Asp Gly Lys His Ile Gln Val Phe Gly Glu Arg Asp
65                  70                  75                  80

Pro Ser Asn Ile Pro Trp Gly Lys Ala Gly Ala Asp Tyr Val Val Glu
                85                  90                  95

Ser Thr Gly Val Phe Thr Gly Lys Glu Ala Ala Ser Ala His Leu Lys
            100                 105                 110

Gly Gly Ala Lys Lys Val Ile Ile Ser Ala Pro Ser Gly Asp Ala Pro
        115                 120                 125

Met Phe Val Val Gly Val Asn Leu Asp Ala Tyr Lys Pro Asp Met Thr
    130                 135                 140

Val Ile Ser Asn Ala Ser Cys Thr Thr Asn Cys Leu Ala Pro Leu Ala
145                 150                 155                 160

Lys Val Val Asn Asp Lys Tyr Gly Ile Ile Glu Gly Leu Met Thr Thr
                165                 170                 175

Val His Ser Ile Thr Ala Thr Gln Lys Thr Val Asp Gly Pro Ser His
            180                 185                 190

Lys Asp Trp Arg Gly Gly Arg Thr Ala Ser Gly Asn Ile Ile Pro Ser
        195                 200                 205

Ser Thr Gly Ala Ala Lys Ala
    210                 215
```

<210> SEQ ID NO 27
<211> LENGTH: 953
<212> TYPE: DNA
<213> ORGANISM: Yarrowia lipolytica

<400> SEQUENCE: 27

```
gcctctgaat actttcaaca agttacaccc ttcattaatt ctcacgtgac acagattatt    60
aacgtctcgt accaaccaca gattacgacc cattcgcagt cacagttcac tagggtttgg   120
gttgcatccg ttgagagcgg tttgttttta accttctcca tgtgctcact caggttttgg   180
gttcagatca aatcaaggcg tgaaccactt tgtttgagga caaatgtgac acaaccaacc   240
agtgtcaggg gcaagtccgt gacaaagggg aagatacaat gcaattactg acagttacag   300
actgcctcga tgccctaacc ttgccccaaa ataagacaac tgtcctcgtt taagcgcaac   360
cctattcagc gtcacgtcat aatagcgttt ggatagcact agtctatgag gagcgtttta   420
tgttgcggtg agggcgattg tgctcatat gggttcaatt gaggtggcgg aacgagctta   480
gtcttcaatt gaggtgcgag cgacacaatt gggtgtcacg tggcctaatt gacctcgggt   540
cgtggagtcc ccagttatac agcaaccacg aggtgcatgg gtaggagacg tcaccagaca   600
ataggttttt ttttggactg gagagggttg ggcaaaagcg ctcaacgggc tgtttgggga   660
gctgtggggg aggaattggc gatatttgtg aggttaacgg ctccgatttg cgtgttttgt   720
cgctcctgca tctccccata cccatatctt ccctccccac ctctttccac gataatttta   780
cggatcagca ataaggttcc ttctcctagt ttccacgtcc atatatatct atgctgcgtc   840 gtcctttcg tgacatcacc aaaacacata caaaaatgcc taaactgatt ctgctgcgac   900
acggccagtc cgactggaac gagaagaacc tgttcaccgg atgggtcgac gtc          953

<210> SEQ ID NO 28
<211> LENGTH: 1537
<212> TYPE: DNA
<213> ORGANISM: Yarrowia lipolytica
<220> FEATURE:
<221> NAME/KEY: misc_feature
<222> LOCATION: (1507)..(1507)
<223> OTHER INFORMATION: n is a, c, g, or t

<400> SEQUENCE: 28
gcctctgaat actttcaaca agttacaccc ttcattaatt ctcacgtgac acagattatt    60
aacgtctcgt accaaccaca gattacgacc cattcgcagt cacagttcac tagggtttgg   120
gttgcatccg ttgagagcgg tttgttttta accttctcca tgtgctcact caggttttgg   180
gttcagatca aatcaaggcg tgaaccactt tgtttgagga caaatgtgac acaaccaacc   240
agtgtcaggg gcaagtccgt gacaaagggg aagatacaat gcaattactg acagttacag   300
actgcctcga tgccctaacc ttgccccaaa ataagacaac tgtcctcgtt taagcgcaac   360
cctattcagc gtcacgtcat aatagcgttt ggatagcact agtctatgag gagcgtttta   420
tgttgcggtg agggcgattg tgctcatat gggttcaatt gaggtggcgg aacgagctta   480
gtcttcaatt gaggtgcgag cgacacaatt gggtgtcacg tggcctaatt gacctcgggt   540
cgtggagtcc ccagttatac agcaaccacg aggtgcatgg gtaggagacg tcaccagaca   600
ataggttttt ttttggactg gagagggttg ggcaaaagcg ctcaacgggc tgtttgggga   660
gctgtggggg aggaattggc gatatttgtg aggttaacgg ctccgatttg cgtgttttgt   720
cgctcctgca tctccccata cccatatctt ccctccccac ctctttccac gataatttta   780
cggatcagca ataaggttcc ttctcctagt ttccacgtcc atatatatct atgctgcgtc   840 gtcctttcg tgacatcacc aaaacacata caaaaatgcc taaactgatt ctgctgcgac   900
acggccagtc cgactggaac gagaagacct gttcaccgga tgggtcgacg tcaagctctc   960
cgagctcggc cacaccgagg ccaagcgagc cggtactctg ctcaaggagt ccggtctcaa  1020
gccccagatt ctctacacct ccgagctctc tcgagccatc cagaccgcca acattgctct  1080
```

```
ggatgaggcc gaccgactgt ggatccccac caagcgatcg tggcgactca acgagcgaca    1140
ctacggcgct ctgcagggca aggacaaggc cgccactctc gccgagtacg gccccgagca    1200
gttccagctc tggcgacgat cttttgacgt ccctcctccc cctatcgctg acgacgacaa    1260
gtggtctcag tacaacgacg agcgatacca ggacatcccc aaggatattc tgcccaagac    1320
cgagtctctg aagctcgtga ttgaccgact ccttccttac tacaactccg acattgtccc    1380
cgaccttaag gccggcaaga ccgtcctcat tgctgcccac ggaaactccc tccgagctct    1440
cgtcaagcac ctcgcggta tctccgatga cgatatcgcc gcccttaaca tccccaccgg    1500
tatcccnctc gtgctacgac cttgatgaca acctcaa                            1537
```

<210> SEQ ID NO 29
<211> LENGTH: 33
<212> TYPE: DNA
<213> ORGANISM: Artificial Sequence
<220> FEATURE:
<223> OTHER INFORMATION: Primer YL33

<400> SEQUENCE: 29

```
tttccatggt acgtcctgta gaaaccccaa ccc                                 33
```

<210> SEQ ID NO 30
<211> LENGTH: 36
<212> TYPE: DNA
<213> ORGANISM: Artificial Sequence
<220> FEATURE:
<223> OTHER INFORMATION: Primer YL34

<400> SEQUENCE: 30

```
cccttaatta atcattgttt gcctccctgc tgcggt                              36
```

<210> SEQ ID NO 31
<211> LENGTH: 19
<212> TYPE: DNA
<213> ORGANISM: Artificial Sequence
<220> FEATURE:
<223> OTHER INFORMATION: Primer TEF5'

<400> SEQUENCE: 31

```
agagaccggg ttggcggcg                                                 19
```

<210> SEQ ID NO 32
<211> LENGTH: 30
<212> TYPE: DNA
<213> ORGANISM: Artificial Sequence
<220> FEATURE:
<223> OTHER INFORMATION: Primer TEF3'

<400> SEQUENCE: 32

```
ttggatcctt tgaatgattc ttatactcag                                     30
```

<210> SEQ ID NO 33
<211> LENGTH: 29
<212> TYPE: DNA
<213> ORGANISM: Artificial Sequence
<220> FEATURE:
<223> OTHER INFORMATION: Primer XPR5'

<400> SEQUENCE: 33

```
tttccgcggc ccgagattcc ggcctcttc                                      29
```

<210> SEQ ID NO 34

```
<211> LENGTH: 31
<212> TYPE: DNA
<213> ORGANISM: Artificial Sequence
<220> FEATURE:
<223> OTHER INFORMATION: Primer XPR3'

<400> SEQUENCE: 34
tttccgcgga cacaatatct ggtcaaattt c                              31

<210> SEQ ID NO 35
<211> LENGTH: 30
<212> TYPE: DNA
<213> ORGANISM: Artificial Sequence
<220> FEATURE:
<223> OTHER INFORMATION: Primer YL1

<400> SEQUENCE: 35
cagtgccaaa agccaaggca ctgagctcgt                                30

<210> SEQ ID NO 36
<211> LENGTH: 31
<212> TYPE: DNA
<213> ORGANISM: Artificial Sequence
<220> FEATURE:
<223> OTHER INFORMATION: Primer YL2

<400> SEQUENCE: 36
gacgagctca gtgccttggc ttttggcact g                              31

<210> SEQ ID NO 37
<211> LENGTH: 36
<212> TYPE: DNA
<213> ORGANISM: Artificial Sequence
<220> FEATURE:
<223> OTHER INFORMATION: Primer YL3

<400> SEQUENCE: 37
gtataagaat cattcaccat ggatccacta gttcta                         36

<210> SEQ ID NO 38
<211> LENGTH: 36
<212> TYPE: DNA
<213> ORGANISM: Artificial Sequence
<220> FEATURE:
<223> OTHER INFORMATION: Primer YL4

<400> SEQUENCE: 38
tagaactagt ggatccatgg tgaatgattc ttatac                         36

<210> SEQ ID NO 39
<211> LENGTH: 36
<212> TYPE: DNA
<213> ORGANISM: Artificial Sequence
<220> FEATURE:
<223> OTHER INFORMATION: Primer YL23

<400> SEQUENCE: 39
atggatccac tagttaatta actagagcgg ccgcca                         36

<210> SEQ ID NO 40
<211> LENGTH: 36
<212> TYPE: DNA
<213> ORGANISM: Artificial Sequence
<220> FEATURE:
<223> OTHER INFORMATION: Primer YL24

<400> SEQUENCE: 40
```

<210> SEQ ID NO 41
<211> LENGTH: 35
<212> TYPE: DNA
<213> ORGANISM: Artificial Sequence
<220> FEATURE:
<223> OTHER INFORMATION: Primer YL9

<400> SEQUENCE: 41
tggtaaataa atgatgtcga ctcaggcgac gacgg        35

<210> SEQ ID NO 42
<211> LENGTH: 35
<212> TYPE: DNA
<213> ORGANISM: Artificial Sequence
<220> FEATURE:
<223> OTHER INFORMATION: Primer YL10

<400> SEQUENCE: 42
ccgtcgtcgc ctgagtcgac atcatttatt tacca        35

<210> SEQ ID NO 43
<211> LENGTH: 971
<212> TYPE: DNA
<213> ORGANISM: Yarrowia lipolytica

<400> SEQUENCE: 43
gacgcagtag gatgtcctgc acgggtcttt ttgtggggtg tggagaaagg ggtgcttgga        60
gatggaagcc ggtagaaccg ggctgcttgt gcttggagat ggaagccggt agaaccgggc       120
tgcttggggg gatttgggc cgctgggctc aaagagggg taggcatttc gttggggtta       180
cgtaattgcg gcatttgggt cctgcgcgca tgtcccattg gtcagaatta gtccggatag       240
gagacttatc agccaatcac agcgccggat ccacctgtag gttgggttgg gtgggagcac       300
ccctccacag agtagagtca aacagcagca gcaacatgat agttgggggt gtgcgtgtta       360
aaggaaaaaa aagaagcttg ggttatattc ccgctctatt tagaggttgc gggatagacg       420
ccgacggagg gcaatggcgc catggaacct tgcggatatc gatacgccgc ggcggactgc       480
gtccgaacca gctccagcag cgttttttcc gggccattga gccgactgcg accccgccaa       540
cgtgtcttgg cccacgcact catgtcatgt tggtgttggg aggccacttt ttaagtagca       600
caaggcacct agctcgcagc aaggtgtccg aaccaaagaa gcggctgcag tggtgcaaac       660
ggggcggaaa cggcgggaaa aagccacggg ggcacgaatt gaggcacgcc ctcgaatttg       720
agacgagtca cggcccattt cgcccgcgca atggctcgcc aacgcccggt cttttgcacc       780
acatcaggtt accccaagcc aaacctttgt gttaaaaagc ttaacatatt ataccgaacg       840
taggtttggg cgggcttgct ccgtctgtcc aaggcaacat ttatataagg gtctgcatcg       900
ccggctcaat tgaatctttt ttcttcttct cttctctata ttcattcttg aattaaacac       960
acatcaacat g                                                            971

<210> SEQ ID NO 44
<211> LENGTH: 878
<212> TYPE: DNA
<213> ORGANISM: Yarrowia lipolytica

<400> SEQUENCE: 44
gcctctgaat actttcaaca agttacaccc ttcattaatt ctcacgtgac acagattatt        60

```
aacgtctcgt accaaccaca gattacgacc cattcgcagt cacagttcac tagggtttgg    120
gttgcatccg ttgagagcgg tttgttttta accttctcca tgtgctcact caggttttgg    180
gttcagatca aatcaaggcg tgaaccactt tgtttgagga caaatgtgac acaaccaacc    240
agtgtcaggg gcaagtccgt gacaaagggg aagatacaat gcaattactg acagttacag    300
actgcctcga tgccctaacc ttgccccaaa ataagacaac tgtcctcgtt taagcgcaac    360
cctattcagc gtcacgtcat aatagcgttt ggatagcact agtctatgag gagcgtttta    420
tgttgcggtg agggcgattg gtgctcatat gggttcaatt gaggtggcgg aacgagctta    480
gtcttcaatt gaggtgcgag cgacacaatt gggtgtcacg tggcctaatt gacctcgggt    540
cgtggagtcc ccagttatac agcaaccacg aggtgcatgg gtaggagacg tcaccagaca    600
ataggttttt ttttggactg gagagggttg ggcaaaagcg ctcaacgggc tgtttgggga    660
gctgtggggg aggaattggc gatatttgtg aggttaacgg ctccgatttg cgtgttttgt    720
cgctcctgca tctccccata cccatatctt ccctccccac ctctttccac gataatttta    780
cggatcagca ataaggttcc ttctcctagt ttccacgtcc atatatatct atgctgcgtc    840
gtccttttcg tgacatcacc aaaacacata caaaaatg                            878
```

<210> SEQ ID NO 45
<211> LENGTH: 30
<212> TYPE: DNA
<213> ORGANISM: Artificial Sequence
<220> FEATURE:
<223> OTHER INFORMATION: Primer YL211

<400> SEQUENCE: 45
tttgtcgacg cagtaggatg tcctgcacgg                                      30

<210> SEQ ID NO 46
<211> LENGTH: 34
<212> TYPE: DNA
<213> ORGANISM: Artificial Sequence
<220> FEATURE:
<223> OTHER INFORMATION: Primer YL212

<400> SEQUENCE: 46
tttccatggt tgatgtgtgt ttaattcaag aatg                                 34

<210> SEQ ID NO 47
<211> LENGTH: 33
<212> TYPE: DNA
<213> ORGANISM: Artificial Sequence
<220> FEATURE:
<223> OTHER INFORMATION: Primer YL203

<400> SEQUENCE: 47
tttccatggt tgtatgtgtt ttggtgatgt cac                                  33

<210> SEQ ID NO 48
<211> LENGTH: 33
<212> TYPE: DNA
<213> ORGANISM: Artificial Sequence
<220> FEATURE:
<223> OTHER INFORMATION: Primer YL204

<400> SEQUENCE: 48
tttgtcgacc gtttaagcgc aaccctattc agc                                  33

<210> SEQ ID NO 49
<211> LENGTH: 39

```
<212> TYPE: DNA
<213> ORGANISM: Artificial Sequence
<220> FEATURE:
<223> OTHER INFORMATION: Primer YL5

<400> SEQUENCE: 49
cccccctcga ggtcgatggt gtcgataagc ttgatatcg                              39

<210> SEQ ID NO 50
<211> LENGTH: 39
<212> TYPE: DNA
<213> ORGANISM: Artificial Sequence
<220> FEATURE:
<223> OTHER INFORMATION: Primer YL6

<400> SEQUENCE: 50
cgatatcaag cttatcgaca ccatcgacct cgaggggggg                             39

<210> SEQ ID NO 51
<211> LENGTH: 37
<212> TYPE: DNA
<213> ORGANISM: Artificial Sequence
<220> FEATURE:
<223> OTHER INFORMATION: Primer YL7

<400> SEQUENCE: 51
caaccgattt cgacagttaa ttataatttt gaatcga                                37

<210> SEQ ID NO 52
<211> LENGTH: 37
<212> TYPE: DNA
<213> ORGANISM: Artificial Sequence
<220> FEATURE:
<223> OTHER INFORMATION: Primer YL8

<400> SEQUENCE: 52
tcgattcaaa ttattaatta actgtcgaaa tcggttg                                37

<210> SEQ ID NO 53
<211> LENGTH: 33
<212> TYPE: DNA
<213> ORGANISM: Artificial Sequence
<220> FEATURE:
<223> OTHER INFORMATION: Primer YL61

<400> SEQUENCE: 53
acaattccac acaacgtacg agccggaagc ata                                    33

<210> SEQ ID NO 54
<211> LENGTH: 33
<212> TYPE: DNA
<213> ORGANISM: Artificial Sequence
<220> FEATURE:
<223> OTHER INFORMATION: Primer YL62

<400> SEQUENCE: 54
tatgcttccg gctcgtacgt tgtgtggaat tgt                                    33

<210> SEQ ID NO 55
<211> LENGTH: 18
<212> TYPE: DNA
<213> ORGANISM: Artificial Sequence
<220> FEATURE:
<223> OTHER INFORMATION: Primer GPDsense

<400> SEQUENCE: 55
```

```
atacgagatc gtcaaggg                                                    18
```

<210> SEQ ID NO 56
<211> LENGTH: 26
<212> TYPE: DNA
<213> ORGANISM: Artificial Sequence
<220> FEATURE:
<223> OTHER INFORMATION: Primer GPDantisense

<400> SEQUENCE: 56

```
gcggccgcgg attgatgtgt gtttaa                                           26
```

<210> SEQ ID NO 57
<211> LENGTH: 1209
<212> TYPE: DNA
<213> ORGANISM: Fusarium monoliforme

<400> SEQUENCE: 57

```
atggcgactc gacagcgaac tgccaccact gttgtggtcg aggaccttcc caaggtcact      60
cttgaggcca agtctgaacc tgtgttcccc gatatcaaga ccatcaagga tgccattccc    120
gcgcactgct ccagccctc  gctcgtcacc tcattctact acgtcttccg cgattttgcc    180
atggtctctg ccctcgtctg ggctgctctc acctacatcc ccagcatccc cgaccagacc    240
ctccgcgtcg cagcttggat ggtctacggc ttcgtccagg gtctgttctg caccggtgtc    300
tggattctcg gccatgagtg cggccacggt gctttctctc tccacggaaa ggtcaacaat    360
gtgaccggct ggttcctcca ctcgttcctc ctcgtcccct acttcagctg gaagtactct    420
caccaccgcc accaccgctt caccggccac atggatctcg acatggcttt cgtccccaag    480
actgagccca gccctccaa gtcgctcatg attgctggca ttgacgtcgc cgagcttgtt    540
gaggacaccc ccgctgctca gatggtcaag ctcatcttcc accagctttt cggatggcag    600
gcgtacctct tcttcaacgc tagctctggc aagggcagca agcagtggga gcccaagact    660
ggcctctcca gtggttccg  agtcagtcac ttcgagccta ccagcgctgt cttccgcccc    720
aacgaggcca tcttcatcct catctccgat atcggtcttg ctctaatggg aactgctctg    780
tactttgctt ccaagcaagt tggtgtttcg accattctct tcctctacct tgttccctac    840
ctgtgggttc accactggct cgttgccatt acctacctcc accaccacca caccgagctc    900
cctcactaca ccgctgaggg ctggacctac gtcaagggag ctctcgccac tgtcgaccgt    960
gagtttggct tcatcggaaa gcacctcttc cacggtatca ttgagaagca cgttgttcac   1020
catctcttcc ctaagatccc cttctacaag gctgacgagg ccaccgaggc catcaagccc   1080
gtcattggcg accactactg ccacgacgac cgaagcttcc tgggccagct gtggaccatc   1140
ttcggcacgc tcaagtacgt cgagcacgac cctgcccgac ccggtgccat gcgatggaac   1200
aaggactag                                                           1209
```

<210> SEQ ID NO 58
<211> LENGTH: 402
<212> TYPE: PRT
<213> ORGANISM: Fusarium monoliforme

<400> SEQUENCE: 58

```
Met Ala Thr Arg Gln Arg Thr Ala Thr Thr Val Val Val Glu Asp Leu
1               5                   10                  15

Pro Lys Val Thr Leu Glu Ala Lys Ser Glu Pro Val Phe Pro Asp Ile
            20                  25                  30

Lys Thr Ile Lys Asp Ala Ile Pro Ala His Cys Phe Gln Pro Ser Leu
```

```
                 35                  40                  45
Val Thr Ser Phe Tyr Tyr Val Phe Arg Asp Phe Ala Met Val Ser Ala
 50                  55                  60

Leu Val Trp Ala Ala Leu Thr Tyr Ile Pro Ser Ile Pro Asp Gln Thr
 65                  70                  75                  80

Leu Arg Val Ala Ala Trp Met Val Tyr Gly Phe Val Gln Gly Leu Phe
                 85                  90                  95

Cys Thr Gly Val Trp Ile Leu Gly His Glu Cys Gly His Gly Ala Phe
                100                 105                 110

Ser Leu His Gly Lys Val Asn Asn Val Thr Gly Trp Phe Leu His Ser
                115                 120                 125

Phe Leu Leu Val Pro Tyr Phe Ser Trp Lys Tyr Ser His His Arg His
                130                 135                 140

His Arg Phe Thr Gly His Met Asp Leu Asp Met Ala Phe Val Pro Lys
145                 150                 155                 160

Thr Glu Pro Lys Pro Ser Lys Ser Leu Met Ile Ala Gly Ile Asp Val
                165                 170                 175

Ala Glu Leu Val Glu Asp Thr Pro Ala Ala Gln Met Val Lys Leu Ile
                180                 185                 190

Phe His Gln Leu Phe Gly Trp Gln Ala Tyr Leu Phe Phe Asn Ala Ser
                195                 200                 205

Ser Gly Lys Gly Ser Lys Gln Trp Glu Pro Lys Thr Gly Leu Ser Lys
                210                 215                 220

Trp Phe Arg Val Ser His Phe Glu Pro Thr Ser Ala Val Phe Arg Pro
225                 230                 235                 240

Asn Glu Ala Ile Phe Ile Leu Ile Ser Asp Ile Gly Leu Ala Leu Met
                245                 250                 255

Gly Thr Ala Leu Tyr Phe Ala Ser Lys Gln Val Gly Val Ser Thr Ile
                260                 265                 270

Leu Phe Leu Tyr Leu Val Pro Tyr Leu Trp Val His His Trp Leu Val
                275                 280                 285

Ala Ile Thr Tyr Leu His His Thr His Thr Glu Leu Pro His Tyr Thr
290                 295                 300

Ala Glu Gly Trp Thr Tyr Val Lys Gly Ala Leu Ala Thr Val Asp Arg
305                 310                 315                 320

Glu Phe Gly Phe Ile Gly Lys His Leu Phe His Gly Ile Ile Glu Lys
                325                 330                 335

His Val Val His His Leu Phe Pro Lys Ile Pro Phe Tyr Lys Ala Asp
                340                 345                 350

Glu Ala Thr Glu Ala Ile Lys Pro Val Ile Gly Asp His Tyr Cys His
                355                 360                 365

Asp Asp Arg Ser Phe Leu Gly Gln Leu Trp Thr Ile Phe Gly Thr Leu
370                 375                 380

Lys Tyr Val Glu His Asp Pro Ala Arg Pro Gly Ala Met Arg Trp Asn
385                 390                 395                 400

Lys Asp

<210> SEQ ID NO 59
<211> LENGTH: 36
<212> TYPE: DNA
<213> ORGANISM: Artificial Sequence
<220> FEATURE:
<223> OTHER INFORMATION: Primer P192

<400> SEQUENCE: 59
```

-continued

| | |
|---|---|
| aaatatgcgg ccgcacaatg gcgactcgac agcgaa | 36 |
| <210> SEQ ID NO 60<br><211> LENGTH: 34<br><212> TYPE: DNA<br><213> ORGANISM: Artificial Sequence<br><220> FEATURE:<br><223> OTHER INFORMATION: Primer P193<br><400> SEQUENCE: 60<br>tttatagcgg ccgcctagtc cttgttccat cgca | 34 |

GLYCERALDEHYDE-3-PHOSPHATE DEHYDROGENASE AND PHOSPHOGLYCERATE MUTASE PROMOTERS FOR GENE EXPRESSION IN OLEAGINOUS YEAST

This application claims the benefit of U.S. Provisional Application No. 60/482,263, filed Jun. 25, 2003.

FIELD OF THE INVENTION

This invention is in the field of biotechnology. More specifically, this invention pertains to promoter regions isolated from *Yarrowia lipolytica* that are useful for gene expression in oleaginous yeast.

BACKGROUND OF THE INVENTION

Oleaginous yeast are defined as those organisms that are naturally capable of oil synthesis and accumulation, wherein oil accumulation ranges from at least about 25% up to about 80% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

The technology for growing oleaginous yeast with high oil content is well developed (for example, see EP 0 005 277B1; Ratledge, C., *Prog. Ind. Microbiol.* 16:119-206 (1982)). And, these organisms have been commercially used for a variety of purposes in the past. For example, various strains of *Yarrowa lipolytica* have historically been used for the manufacture and production of: isocitrate lyase (DD259637); lipases (SU1454852, WO2001083773, DD279267); polyhydroxyalkanoates (WO2001088144); citric acid (RU2096461, RU2090611, DD285372, DD285370, DD275480, DD227448, PL160027); erythritol (EP770683); 2-oxoglutaric acid (DD267999); γ-decalactone (U.S. Pat. No. 6,451,565, FR2734843); γ-dodecalactone (EP578388); and pyruvic acid (JP09252790). Most recently, however, the natural abilities of oleaginous yeast have been enhanced by advances in genetic engineering, resulting in organisms capable of producing polyunsaturated fatty acids ("PUFAs"). Specifically, Picataggio et al. have demonstrated that *Yarrowia lipolytica* can be engineered for production of ω-3 and ω-6 fatty acids, by introducing and expressing genes encoding the ω-3/ω-6 biosynthetic pathway (co-pending U.S. patent application Ser. No. 10/840,579).

Recombinant production of any heterologous protein is generally accomplished by constructing an expression cassette in which the DNA coding for the protein of interest is placed under the control of a promoter suitable for the host cell. The expression cassette is then introduced into the host cell (usually by plasmid-mediated transformation or targeted integration into the host genome) and production of the heterologous protein is achieved by culturing the transformed host cell under conditions necessary for the proper function of the promoter contained within the expression cassette. Thus, the development of new host cells (e.g., oleaginous yeast) for recombinant production of proteins generally requires the availability of promoters that are suitable for controlling the expression of a protein of interest in the host cell.

A variety of strong promoters have been isolated from *Saccharomyces cerevisiae* that are useful for heterologous gene expression in yeast. For example, a glyceraldehyde-3-phosphate dehydrogenase (GPD) promoter was described by Bitter, G. A., and K. M. Egan (*Gene* 32(3):263-274 (1984)); and, a phosphoglycerate mutase (GPM1) promoter was investigated by Rodicio, R. et al. (*Gene* 125(2): 125-133 (1993)). Several promoters have also been isolated from *Yarrowia lipolytica* that have been suitable for the recombinant expression of proteins. For example, U.S. Pat. No. 4,937,189 and EP220864 (Davidow et al.) disclose the sequence of the XPR2 gene (which encodes an inducible alkaline extracellular protease) and upstream promoter region for use in expression of heterologous proteins. However, this promoter is only active at a pH above 6.0 on media lacking preferred carbon and nitrogen sources; and full induction requires high levels of peptone in the culture media. Subsequent analysis of the XPR2 promoter sequence by Blanchin-Roland, S. et al. (EP832258; *Mol. Cell Biol.* 14(1):327-338 (1994)) determined that hybrid promoters containing only parts of the XPR2 promoter sequence may be used to obtain high level expression in *Yarrowia*, without the limitations resulting from use of the complete promoter sequence.

U.S. Pat. No. 6,265,185 (Muller et al.) describe yeast promoters from *Yarrowia lipolytica* for the translation elongation factor EF1-α (TEF) protein and ribosomal protein S7 that are suitable for expression cloning in yeast and heterologous expression of proteins. These promoters were improved relative to the XPR2 promoter, when tested for yeast promoter activity on growth plates (Example 9, U.S. Pat. No. 6,265,185) and based on their activity in the pH range of 4-11.

Despite the utility of these known promoters, however, there is a need for new improved yeast promoters for metabolic engineering of yeast (oleaginous and non-oleaginous) and for controlling the expression of heterologous genes in yeast. Furthermore, possession of a suite of promoters that are regulatable under a variety of natural growth and induction conditions in yeast will play an important role in industrial settings, wherein it is desirable to express heterologous polypeptides in commercial quantities in said hosts for economical production of those polypeptides. Thus, it is an object of the present invention to provide such promoters that will be useful for gene expression in a variety of yeast cultures, and preferably in *Yarrowia* sp. cultures and other oleaginous yeast.

Applicants have solved the stated problem by identifying genes encoding a glyceraldehyde-3-phosphate dehydrogenase (GPD) and a phosphoglycerate mutase (GPM) from *Yarrowia lipolytica* and the promoters responsible for driving expression of these native genes. Both promoters are useful for expression of heterologous genes in *Yarrowia* and have improved activity with respect to the TEF promoter.

SUMMARY OF THE INVENTION

The present invention provides methods for the expression of a coding region of interest in a transformed yeast cell, using a promoter of the glyceraldehyde-3-phosphate dehydrogenase (gpd) or phosphoglycerate mutase (gpm) genes. Accordingly, the present invention provides a method for the expression of a coding region of interest in a transformed yeast cell comprising:

a) providing a transformed yeast cell having a chimeric gene comprising:

(i) a promoter region of a *Yarrowia* gene selected from the group consisting of: a gpm gene and a gpd gene; and
(ii) a coding region of interest expressible in the yeast cell;
wherein the promoter region is operably linked to the coding region of interest; and
b) growing the transformed yeast cell of step (a) under conditions whereby the chimeric gene of step (a) is expressed.

In a preferred embodiment the invention provides a method for the production of an ω-3 or an ω-6 fatty acid comprising:
a) providing a transformed oleaginous yeast comprising a chimeric gene, comprising:
(i) a promoter region of a *Yarrowia* gene selected from the group consisting of: a gpm gene and a gpd gene; and
(ii) a coding region encoding at least one enzyme of the ω-3/ω-6 fatty acid biosynthetic pathway;
wherein the promoter region and coding region are operably linked; and
(b) contacting the transformed oleaginous yeast of step (a) under conditions whereby the at least one enzyme of the ω-3/ω-6 fatty biosynthetic pathway is expressed and a ω-3 or ω-6 fatty acid is produced; and
(c) optionally recovering the ω-3 or ω-6 fatty acid.

Additionally the invention provides an isolated nucleic acid molecule comprising a gpd promoter selected from the group consisting of SEQ ID NO:23, SEQ ID NO:24 and SEQ ID NO:43.

In similar fashion the invention provides an isolated nucleic acid molecule comprising a gpm promoter selected from the group consisting of SEQ ID NO:27, SEQ ID NO:28 and SEQ ID NO:44.

BRIEF DESCRIPTION OF THE DRAWINGS AND SEQUENCE DESCRIPTIONS

FIGS. 1A and 1B shows an alignment of known glyceraldehyde-3-phosphate dehydrogenase (GPD) proteins from *Saccharomyces cerevisiae* (GenBank Accession No. CM24607), *Schizosaccharomyces pombe* (GenBank Accession No. NP_595236), *Aspergillus oryzae* (GenBank Accession No. MK08065), *Paralichthys olivaceus* (GenBank Accession No. BM88638), *Xenopus laevis* (GenBank Accession No. P51469) and *Gallus gallus* (GenBank Accession No. DECHG3), used to identify two conserved regions within the sequence alignment.

FIG. 2 shows an alignment of amino acids encoding portions of the GPD protein from *Yarrowia lipolytica*, *Schizosaccharomyces pombe*, *Gallus gallus* and *Xenopus laevis*.

FIG. 3 shows an alignment of phosphoglycerate mutase (GPM) proteins from *Yarrowia lipolytica* and *Saccharomyces cerevisiae*.

Figure 4:
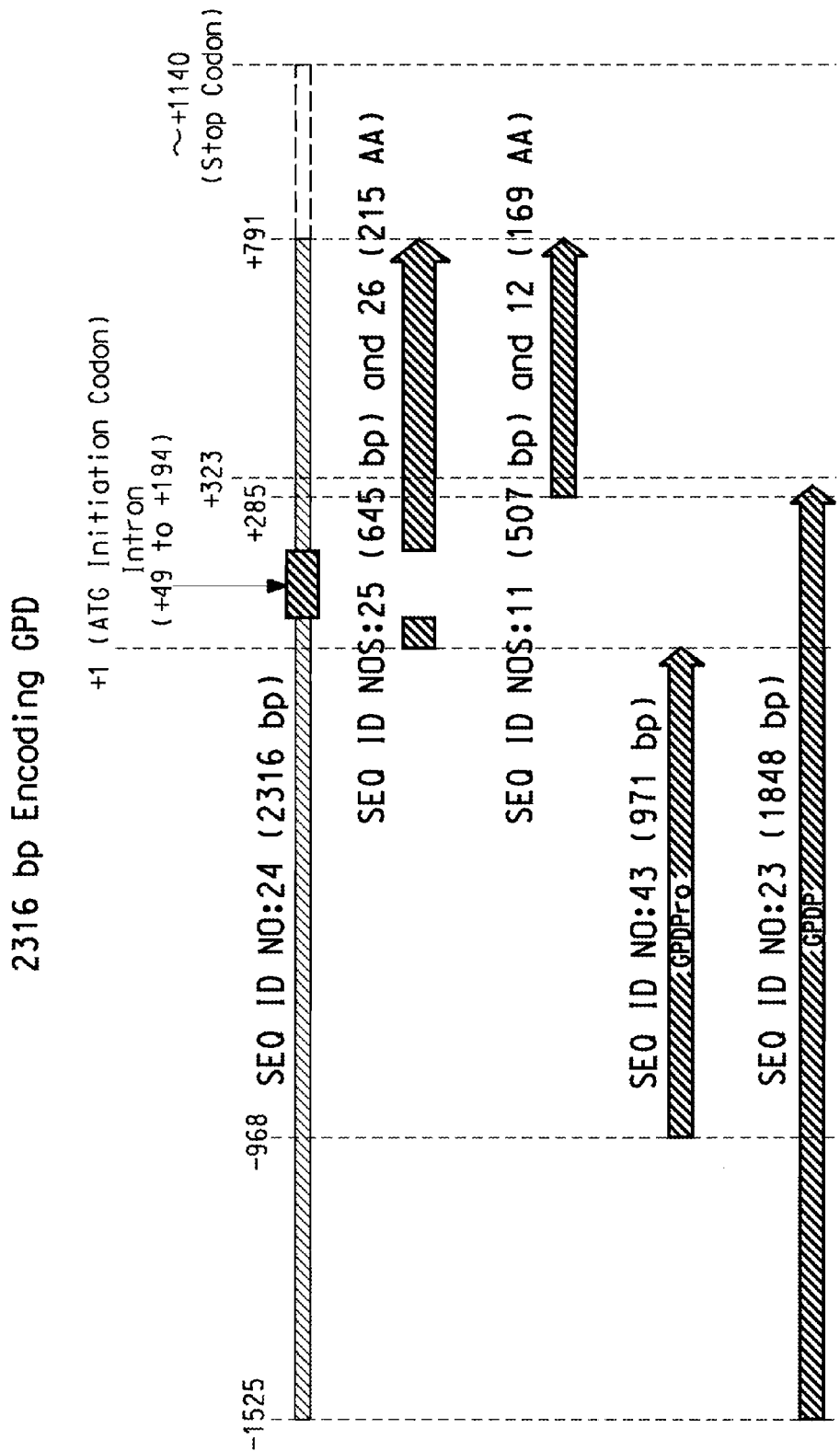

FIG. 4 graphically represents the relationship between SEQ ID NOs:11, 12, 23-26 and 43, each of which relates to glyceraldehyde-3-phosphate dehydrogenase (GPD) in *Yarrowia lipolytica*.

Figure 5:
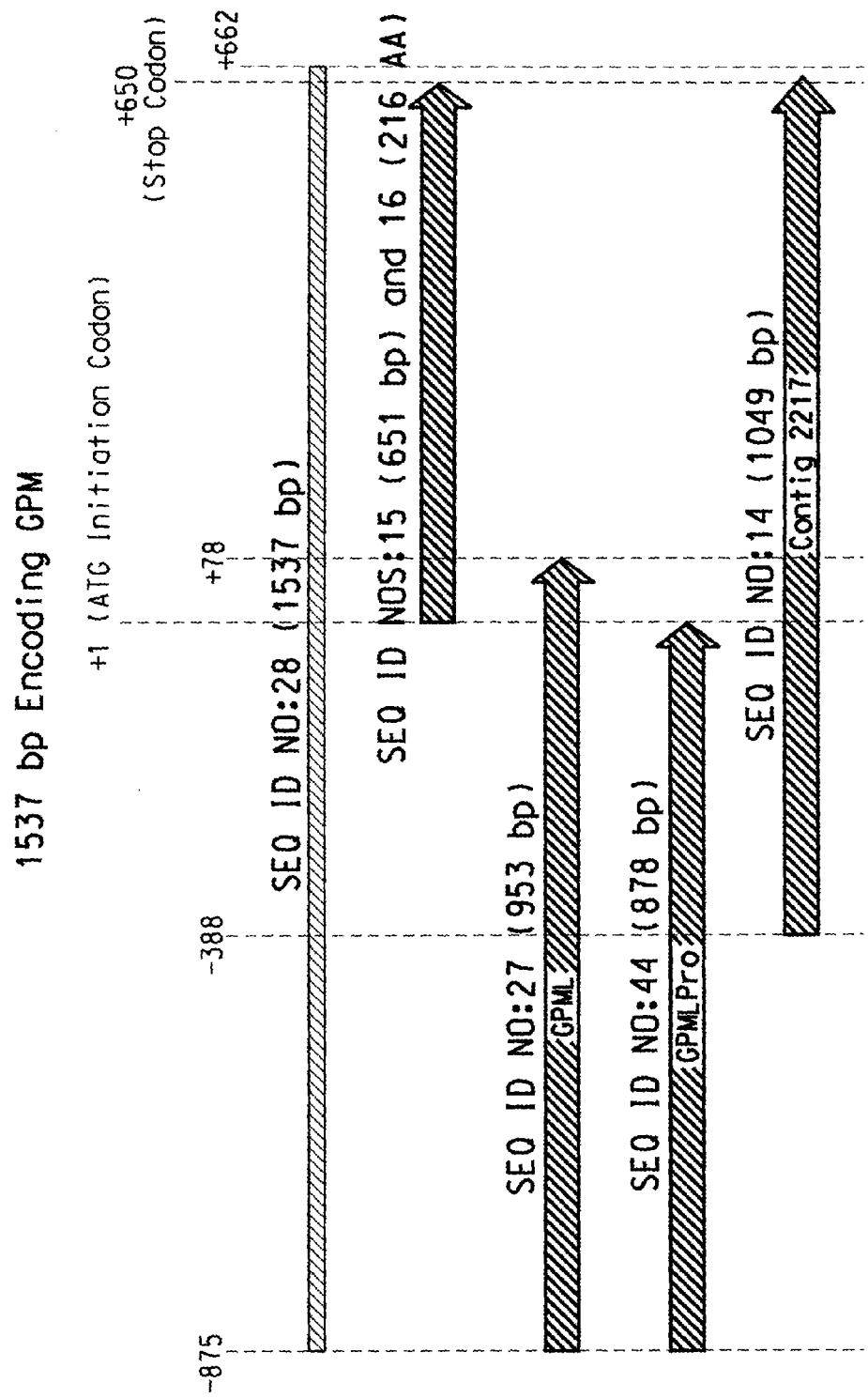

FIG. 5 graphically represents the relationship between SEQ ID NOs:14-16, 27, 28 and 44, each of which relates to phosphoglycerate mutase (GPM) in *Yarrowia lipolytica*.

Figure 6B:
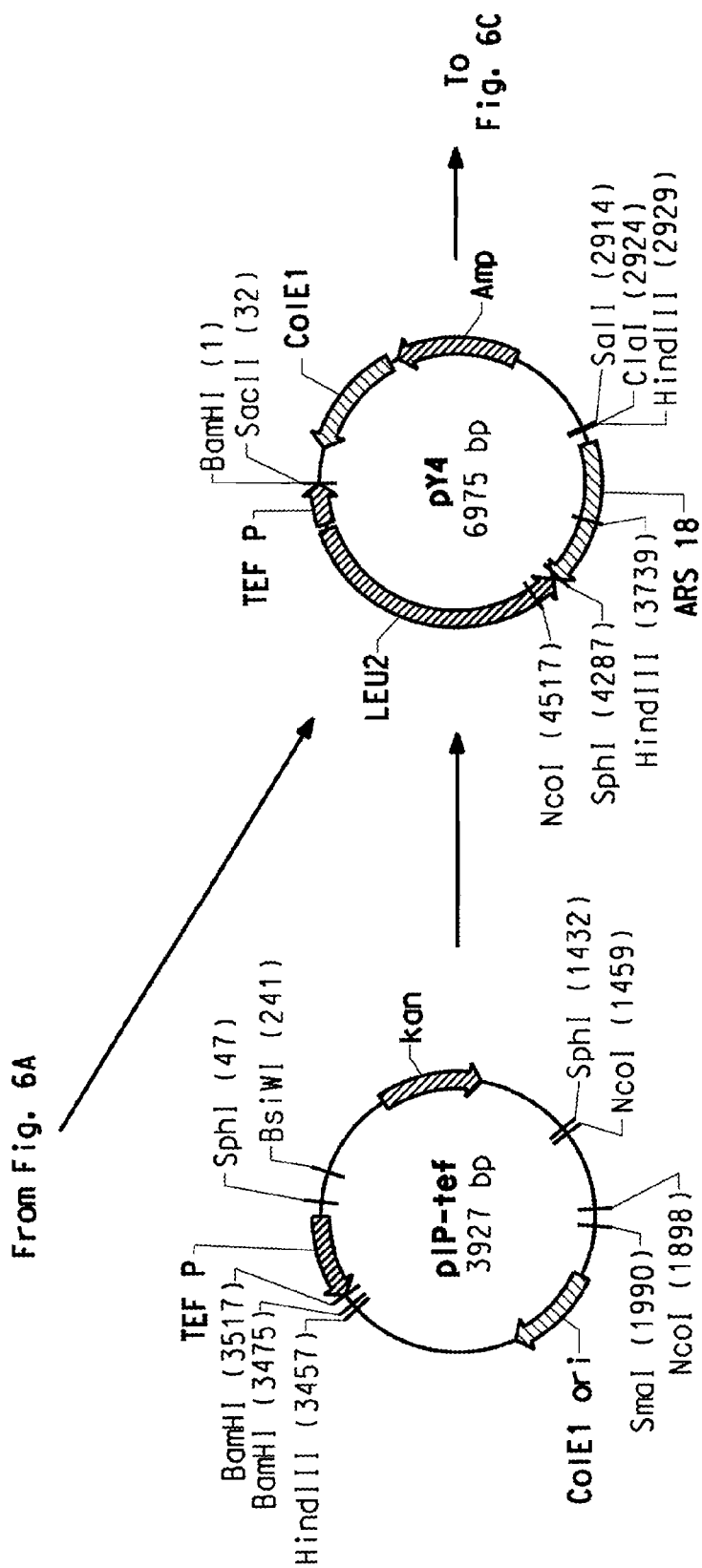

FIG. 6 illustrates the construction of plasmid vector pY5-4.

FIGS. 7A, 7B, 7C and 7D provide plasmid maps for pY5-10, pY5-30, pYZGDG and pYZGMG, respectively.

Figure 8A:
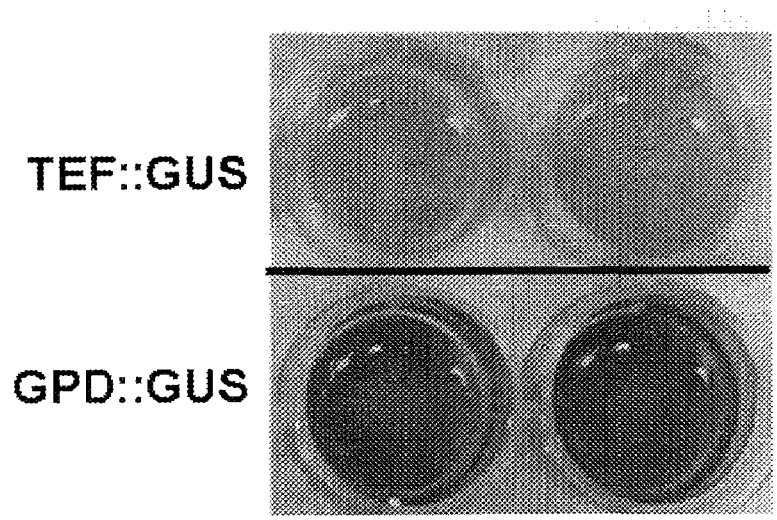
Figure 8B:
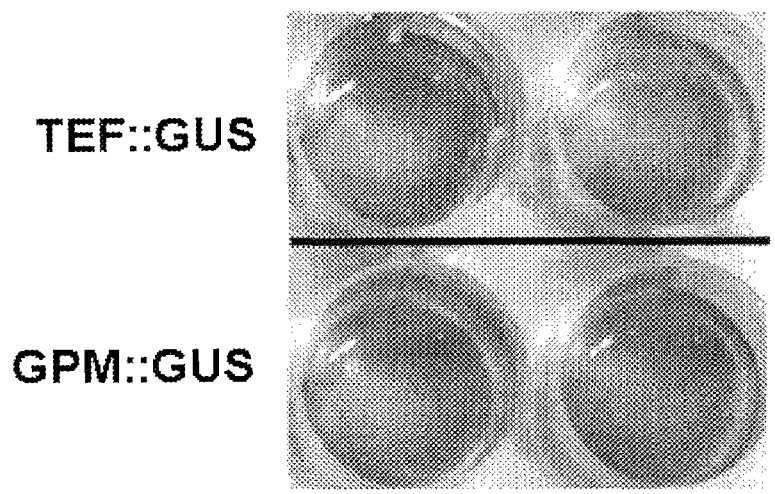

FIG. 8A is an image of a cell culture comparing the promoter activity of TEF and GPD in *Yarrowia lipolytica* as determined by histochemical staining. FIG. 8B is an image of a cell culture comparing the promoter activity of TEF and GPM in *Y. lipolytica* as determined by histochemical staining.

Figure 9A:
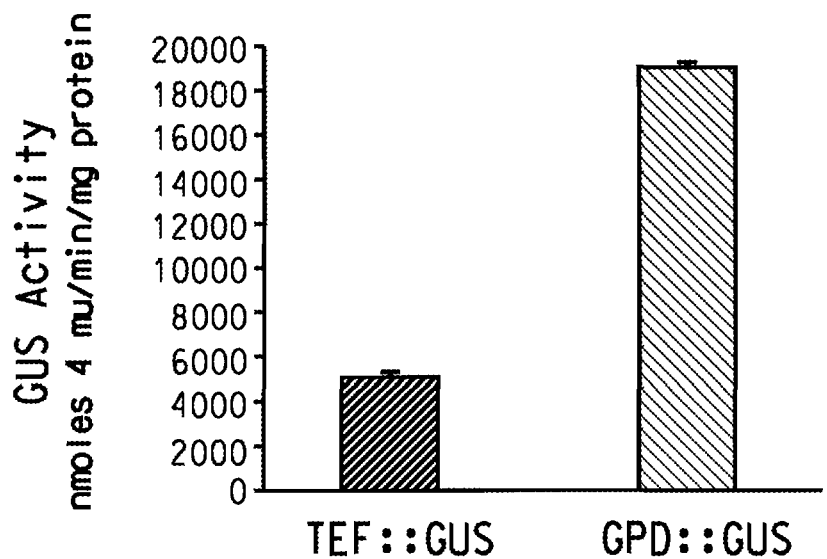
Figure 9B:
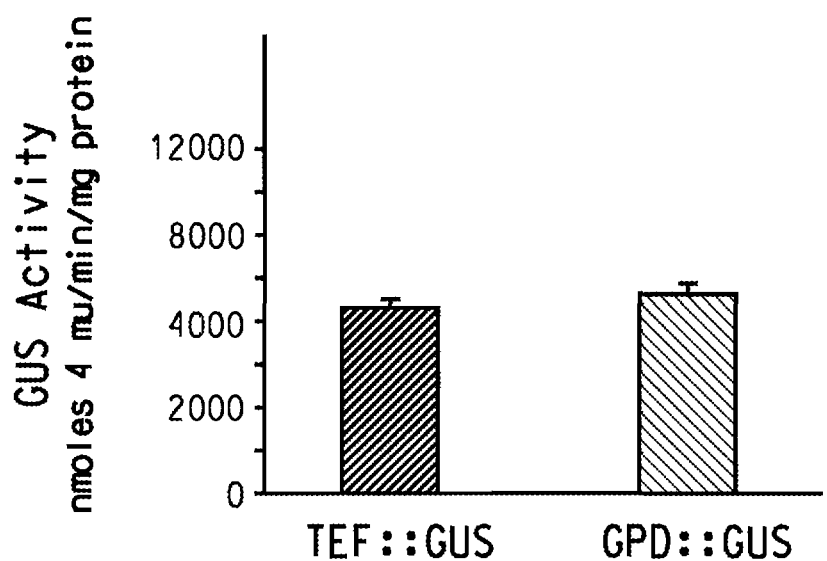

FIG. 9A is a graph comparing the promoter activity of TEF and GPD as determined fluorometically. FIG. 9B is a graph comparing the promoter activity of TEF and GPM as determined fluorometically.

Figure 10:
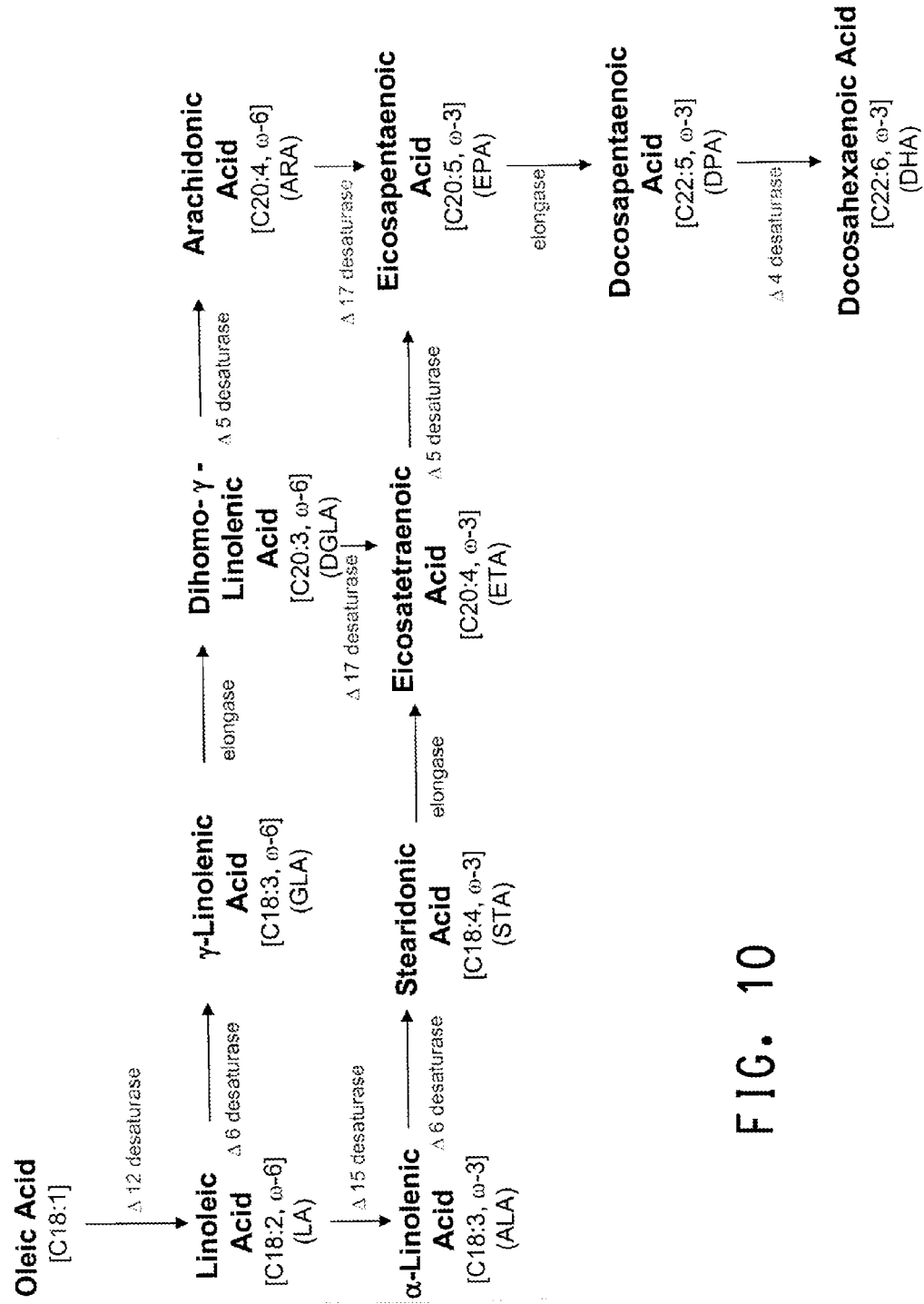

FIG. 10 illustrates the ω-3/ω-6 fatty acid biosynthetic pathway.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-6 correspond to the GPD amino acid sequences of *Saccharomyces cerevisiae* (GenBank Accession No. CM24607), *Schizosaccharomyces pombe* (GenBank Accession No. NP_595236), *Aspergillus oryzae* (GenBank Accession No. AAK08065), *Paralichthys olivaceus* (GenBank Accession No. BM88638), *Xenopus laevis* (GenBank Accession No. P51469) and *Gallus gallus* (GenBank Accession No. DECHG3), respectively.

SEQ ID NOs:7 and 8 correspond to conserved amino acid regions of the GPD protein.

SEQ ID NOs:9 and 10 correspond to the degenerate primers YL193 and YL194, respectively, used for isolating an internal portion of the *Yarrowia lipolytica* GPD gene.

SEQ ID NO:11 encodes a 507 bp internal portion of the *Yarrowia lipolytica* GPD gene, while SEQ ID NO:12 is the corresponding amino acid sequence.

SEQ ID NO:13 corresponds to the *Saccharomyces cerevisiae* GPM protein (GenBank Accession No. NP_012770).

SEQ ID NO:14 corresponds to Contig 2217, comprising the complete nucleotide coding sequence for the *Yarrowia lipolytica* GPM protein.

SEQ ID NO:15 corresponds to the deduced nucleotide sequence of the *Yarrowia lipolytica* GPM coding region, while SEQ ID NO:16 corresponds to the amino acid sequence.

SEQ ID NOs:17-22 correspond to primers YL206, YL196, YL207, YL197, YL208 and YL198, respectively, used for genome walking.

SEQ ID NO:23 corresponds to a 1848 bp fragment designated as "GPDP", comprising 1525 bp upstream of the GPD gene and an additional 323 bp representing a 5' portion of the GPD gene in *Yarrowia lipolytica*.

SEQ ID NO:24 corresponds to an assembled 2316 bp contig of DNA, corresponding to the −1525 to +791 region of the GPD gene, wherein the 'A' position of the 'ATG' translation initiation codon is designated as +1.

SEQ ID NO:25 corresponds to a partial cDNA sequence encoding the *Yarrowia lipolytica* GPD gene, while SEQ ID NO:26 is the corresponding amino acid sequence.

SEQ ID NO:27 corresponds to a 953 bp fragment designated as "GPML", corresponding to the −875 to +78 region of the GPM gene, wherein the 'A' position of the 'ATG' translation initiation codon is designated as +1.

SEQ ID NO:28 corresponds to an assembled 1537 bp contig of DNA, corresponding to the −875 to +662 region of the GPM gene, wherein the 'A' position of the 'ATG' translation initiation codon is designated as +1.

SEQ ID NOs:29 and 30 correspond to primers YL33 and YL34, respectively, used for amplifying the reporter gene GUS.

SEQ ID NOs:31 and 32 correspond to primers TEF5' and TEF3', respectively, used to isolate the TEF promoter.

SEQ ID NOs:33 and 34 correspond to primers XPR5' and XPR3', respectively, used to isolate the XPR2 transcriptional terminator.

SEQ ID NOs:35-42 correspond to primers YL1, YL2, YL3, YL4, YL23, YL24, YL9 and YL10, respectively, used for site-directed mutagenesis during construction of the pY5-10 plasmid.

SEQ ID NO:43 corresponds to a 971 bp fragment designated as "GPDPro", and identified herein as the putative GPD promoter in *Yarrowia lipolytica*. This fragment corresponds to the −968 to +3 region of the GPD gene, wherein the 'A' position of the 'ATG' translation initiation codon is designated as +1.

SEQ ID NO:44 corresponds to a 878 bp fragment designated as "GPMLPro", and identified herein as the putative GPM promoter in *Yarrowia lipolytica*. This fragment corresponds to the −875 to +3 region of the GPM gene, wherein the 'A' position of the 'ATG' translation initiation codon is designated as +1.

SEQ ID NOs:45 and 46 correspond to primers YL211 and YL212, respectively, used to amplify the putative GPD promoter.

SEQ ID NOs:47 and 48 correspond to primers YL203 and YL204, respectively, used to amplify the putative GPM promoter.

SEQ ID NOs:49-54 correspond to primers YL5, YL6, YL7, YL8, YL61 and YL62, respectively, used for construction of plasmid pY5-13.

SEQ ID NOs:55 and 56 correspond to primers GPDsense and GPDantisense, respectively, used to amplify GPDPro.

SEQ ID NO:57 corresponds to the nucleotide sequence of the *Fusarium moniliforme* strain M-8114 Δ15 desaturase coding region, while SEQ ID NO:58 corresponds to the amino acid sequence.

SEQ ID NOs:59 and 60 correspond to primers P192 and P193, respectively, used to amplify the *F. moniliforme* Δ15 desaturase.

DETAILED DESCRIPTION OF THE INVENTION

In accordance with the subject invention, Applicants describe the isolation and characterization of promoters and genes from an oleaginous yeast, *Yarrowia lipolytica*. These promoter regions, isolated upstream of the glyceraldehyde-3-phosphate dehydrogenase (GPD) and phosphoglycerate mutase (GPM) genes, are useful for genetic engineering in *Y. lipolytica* and other yeast for the production of heterologous polypeptides.

Preferred heterologous polypeptides of the present invention are those that are involved in the synthesis of microbial oils and particularly polyunsaturated fatty acids (PUFAs). PUFAs, or derivatives thereof, made by the methodology disclosed herein can be used in many applications. For example, the PUFAs can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products, and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Thus, the present invention advances the art by providing methods for the expression of a coding region of interest in a transformed yeast comprising: a) providing a transformed yeast cell having a chimeric gene comprising (i) a promoter region of a gpd gene or gpm gene; and (ii) a coding region of interest expressible in the host cell, wherein the promoter region is operably linked to the coding region of interest; and b) growing the transformed yeast cell of step (a) in the presence of a fermentable carbon source, wherein the chimeric gene is expressed and optionally isolated from the cultivation medium. In preferred embodiments, the promoter region comprises a sequence selected from the group consisting of SEQ ID NOs: 23, 24, 27, 28, 43 and 44.

Definitions

In this disclosure, a number of terms and abbreviations are used. The following definitions are provided.

"Glyceraldehyde-3-phosphate dehydrogenase" is abbreviated GPD.

"Phosphoglycerate mutase" is abbreviated GPM.

"Open reading frame" is abbreviated ORF.

"Polymerase chain reaction" is abbreviated PCR.

"Polyunsaturated fatty acid(s)" is abbreviated PUFA(s).

The term "oleaginous" refers to those organisms that tend to store their energy source in the form of lipid (Weete, In: Fungal Lipid Biochemistry, $2^{nd}$ Ed., Plenum, 1980). Generally, the cellular PUFA content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)).

The term "oleaginous yeast" refers to those microorganisms classified as yeast that can accumulate at least 25% of their dry cell weight as oil. Examples of oleaginous yeast include (but are no means limited to) the following genera: *Yarrowia, Candida, Rhodotorula, Rhodosporidium, Cryptococcus, Trichosporon* and *Lipomyces*.

The term "fermentable carbon source" will refer to a carbon source that a microorganism will metabolize to derive energy. Typical carbon sources for use in the present invention include, but are not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

The term "GPD" refers to a glyceraldehyde-3-phosphate dehydrogenase enzyme (E.C. 1.2.1.12) encoded by the gpd gene and which converts D-glyceraldehyde 3-phosphate to 3-phospho-D-glyceroyl phosphate during glycolysis. The partial coding region of a respresentative gpd gene isolated from *Yarrowia lipolytica* is provided as SEQ ID NOs:25 and 26; specifically, the sequence lacks ~115 amino acids that encode the C-terminus of the gene (based on alignment with other known gpd sequences).

The term "GPD promoter" or "GPD promoter region" refers to the 5' upstream untranslated region in front of the 'ATG' translation initiation codon of GPD and that is necessary for expression. Examples of suitable GPD promoter regions are provided as SEQ ID NOs:23 and 43, but these are not intended to be limiting in nature.

The term "GPM" refers to a phosphoglycerate mutase enzyme (EC 5.4.2.1) encoded by the gpm gene and which is responsible for the interconversion of 3-phosphoglycerate and 2-phosphoglycerate during glycolysis. A respresentative gpm gene from *Saccharomyces cerevisiae* is GenBank Accession No. NP_012770 (SEQ ID NO:13); a gpm gene isolated from *Yarrowia lipolytica* is provided as SEQ ID NO:15.

The term "GPM promoter" or "GPM promoter region" refers to the 5' upstream untranslated region in front of the 'ATG' translation initiation codon of GPM and that is necessary for expression. Examples of suitable GPM promoter regions are provided as SEQ ID NOs:27 and 44, but these are not intended to be limiting in nature.

The term "promoter activity" will refer to an assessment of the transcriptional efficiency of a promoter. This may, for instance, be determined directly by measurement of the amount of mRNA transcription from the promoter (e.g., by Northern blotting or primer extension methods) or indirectly by measuring the amount of gene product expressed from the promoter.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to specifically identify and/or isolate a nucleic acid molecule comprising the sequence.

The instant specification teaches partial or complete amino acid and nucleotide sequences encoding one or more particular microbial proteins and promoters. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "oligonucleotide" refers to a nucleic acid, generally of at least 18 nucleotides, that is hybridizable to a genomic DNA molecule, a cDNA molecule, or an mRNA molecule. In one embodiment, a labeled oligonucleotide can be used as a "probe" to detect the presence of a nucleic acid according to the invention. Thus, the term "probe" refers to a single-stranded nucleic acid molecule that can base pair with a complementary single-stranded target nucleic acid to form a double-stranded molecule. The term "label" will refer to any conventional molecule which can be readily attached to mRNA or DNA and which can produce a detectable signal, the intensity of which indicates the relative amount of hybridization of the labeled probe to the DNA fragment.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid moleclues that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Proiects* (Smith, D. W., Ed.) Academic: NY (1993); 3.) *Computer Analysis of Sequence Data, Part I* (Griffin, A. M., and Griffin, H. G., Eds.) Humana: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*. 5:151-153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid molecules (isolated polynucleotides of the present invention) encode polypeptides that are at least about 70% identical, preferably at least about 75% identical, and more preferably at least about 80% identical to the amino acid sequences reported herein. Preferred nucleic acid molecules encode amino acid sequences that are about 85% identical to the amino acid sequences reported herein. More preferred nucleic acid molecules encode amino acid sequences that are at least about 90% identical to the amino acid sequences reported herein. Most preferred are nucleic acid molecules that encode amino acid sequences that are at least about 95% identical to the amino acid sequences reported herein. Suitable nucleic acid molecules not only have the above homologies but typically encode a polypeptide having at least 50 amino acids, preferably at least 100 amino acids, more preferably at least 150 amino acids, still more preferably at least 200 amino acids, and most preferably at least 250 amino acids.

Likewise, suitable promoter regions (isolated polynucleotides of the present invention) encode promoter regions that are at least about 70% identical, preferably at least about 75% identical, and more preferably at least about 80% identical to the nucleotide sequences reported herein. Preferred nucleic acid molecules are about 85% identical to the nucleotide sequences reported herein, more preferred nucleic acid molecules are at least about 90% identical, and most preferred are nucleic acid molecules at least about 95% identical to the nucleotide sequences reported herein. Suitable promoter regions not only have the above homologies but typically are at least 50 nucleotides in length, more preferably at least 100 nucleotides in length, more preferably at least 250 nucleotides in length, and more preferably at least 500 nucleotides in length.

"Codon degeneracy" refers to the nature in the genetic code permitting variation of the nucleotide sequence without affecting the amino acid sequence of an encoded polypeptide. Accordingly, the instant invention relates to any nucleic acid molecule that encodes all or a substantial portion of the amino acid sequence encoding the instant microbial polypeptides as set forth in SEQ ID NOs:16 and 26. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures; or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes of the present invention will typically comprise a GPD or GPM promoter region operably linked to a coding region of interest. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence.

"Suitable regulatory sequences" refer to transcriptional and translational nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "mutant promoter" is defined herein as a promoter having a nucleotide sequence comprising a substitution, deletion, and/or insertion of one or more nucleotides relative to the parent promoter, wherein the mutant promoter has more or less promoter activity than the corresponding parent promoter. The term "mutant promoter" will encompass natural variants and in vitro generated variants obtained using methods well known in the art (e.g., classical mutagenesis, site-directed mutagenesis and "DNA shuffling").

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid molecule so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a coding sequence. Expression may also refer to translation of mRNA into a polypeptide.

"Introns" are sequences of non-coding DNA found in gene sequences (either in the coding region, 5' non-coding region, or 3' non-coding region) in most eukaryotes. Their full function is not known; however, some enhancers are located in the introns (Giacopelli F. et al., *Gene Expr.* 11:95-104 (2003)). These intron sequences are transcribed, but removed from within the pre-mRNA transcript before the mRNA is translated into a protein. This process of intron removal occurs by self-splicing of the sequences (exons) on either side of the intron.

The term "altered biological activity" will refer to an activity, associated with a protein encoded by a nucleotide sequence which can be measured by an assay method, where that activity is either greater than or less than the activity associated with the native sequence. "Enhanced biological activity" refers to an altered activity that is greater than that associated with the native sequence. "Diminished biological activity" is an altered activity that is less than that associated with the native sequence.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid molecules are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403410 (1990)); 3.) DNASTAR (DNASTAR, Inc. Madison, Wis.); and 4.) the FASTA program incorporating the Smith-Waterman algorithm (W. R. Pearson, *Comput. Methods Genome Res.*, [Proc. Int. Symp.] (1994), Meeting Date 1992, 111-20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, 2nd ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Identification of the gpd and qpm Genes in *Yarrowia lipolytica*

The present invention identifies the partial sequence of a glyceraldehyde-3-phosphate dehydrogenase (gpd) gene (wherein ~115 amino acids of the C-terminus of the encoded protein are not disclosed herein) and the complete sequence of the phosphoglycerate mutase (gpm) gene contained within the *Yarrowia lipolytica* genome.

Comparison of the partial gpd nucleotide base and deduced amino acid sequences (SEQ ID NOs:25 and 26) to public databases reveals that the most similar known sequences are about 81% identical to the amino acid sequence of gpd reported herein over a length of 215 amino acids using a Smith-Waterman alignment algorithm (W. R. Pearson, supra). Preferred amino acid fragments are at least about 70%-80% identical to the sequences herein, where those sequences that are 85%-90% identical are particularly suitable and those sequences that are about 95% identical are most preferred. Similarly, preferred gpd encoding nucleic acid sequences corresponding to the instant ORF are those encoding active proteins and which are at least about 70%-80% identical to the nucleic acid sequences of gpd reported herein, where those sequences that are 85%-90% identical are particularly suitable and those sequences that are about 95% identical are most preferred.

Comparison of the gpm nucleotide base and deduced amino acid sequences (SEQ ID NOs:15 and 16) to public databases reveals that the most similar known sequences are about 71% identical to the amino acid sequence of gpm reported herein over a length of 216 amino acids using a Smith-Waterman alignment algorithm (W. R. Pearson, supra). Preferred amino acid fragments are at least about 70%-80% identical to the sequences herein, where those sequences that are 85%-90% identical are particularly suitable and those sequences that are about 95% identical are most preferred. Similarly, preferred gpm encoding nucleic acid sequences corresponding to the instant ORF are those encoding active proteins and which are at least about 70%-80% identical to the nucleic acid sequences of gpm reported herein, where those sequences that are 85%-90% identical are particularly suitable and those sequences that are about 95% identical are most preferred.

Identification of Natural Promoter Regions in *Yarrowia lipolytica*

The present invention also identifies putative promoter regions that naturally regulate GPD and GPM in *Yarrowia lipolytica*. These putative promoter regions have been identified as useful for driving expression of any suitable coding region of interest in a transformed yeast cell.

In the context of the presention invention, a promoter useful in an oleaginous yeast should meet the following criteria:

1.) Strength. A strong yeast promoter is a necessary premise for a high expression level, and the low copy number of the arsl8 (Fournier, P. et al. *Yeast* 7:25-36 (1991)) based expression vectors or chimeric genes integrated into the genome makes this demand even more imporant when *Y. lipolytica* is used as the host organism.
2.) Activity in a medium suitable for expression of the coding region of interest, and high enzymatic activity of that coding region of interest.
3.) pH Tolerance. If the coding region of interest is known to be produced only in e.g., an acidic environment, then the promoter operably linked to said coding region of interest must function at the appropriate pH. pH tolerance is of course limited by the tolerance of the host organism.
4.) Inducibility. A tightly regulated yeast promoter makes it possible to separate the growth stage from the expression stage, thereby enabling expression of products that are known to inhibit cell growth.
5.) Activity in the stationary phase of growth in oleaginous yeast hosts for accumulation of PUFAs.

Additionally, it is preferable for novel yeast promoters to possess differences in activity with respect to the known *Yarrowia lipolytica* TEF and/or XPR2 promoters (U.S. Pat. No. 4,937,189; EP220864; EP832258; U.S. Pat. No. 6,265, 185). A comparative study of the TEF promoter and the GPD and GPM promoters of the instant invention is provided in Example 7. It is shown that the yeast promoters of the invention have improved activity compared to the TEF promoter. The promoter region of the instant GPD gene is contained within several nucleic acid molecules, specifically, SEQ ID NOs: 23, 24 and 43. In one embodiment, the GPD promoter will comprise nucleotides −500 to +1 of SEQ ID NO:43 (wherein the 'A' position of the 'ATG' translation initiation codon is designated as +1), thereby permitting relatively strong promoter activity; in alternate embodiments, the −100 to +1 region of SEQ ID NO:43 should be sufficient for basal activity of the promoter.

The GPM promoter region of the instant invention is contained in several nucleic acid molecules disclosed herein, including SEQ ID NOs:27, 28 and 44. In one embodiment, the GPM promoter will comprise nucleotides −500 to +1 of SEQ ID NO:44 (wherein the 'A' position of the 'ATG' translation initiation codon is designated as +1), thereby permitting relatively strong promoter activity; alternatively, the −100 to +1 region of SEQ ID NO:44 should be sufficient for basal activity of the promoter.

The promoter regions of the invention may comprise additional nucleotides to those specified above. For example, the promoter sequences of the invention may be constructed on the basis of the DNA sequence presented as SEQ ID NO:23 or SEQ ID NO:27 (SEQ ID NOs:43 and 44 are subsequences thereof, respectively). It should be recognized that promoter fragments of various diminishing lengths may have identical promoter activity, since the exact boundaries of the regulatory sequences have not been completely defined.

In alternate embodiments mutant promoters may be constructed, wherein the DNA sequence of the promoter has one or more nucleotide substitutions (i.e., deletions, insertions, substitutions, or addition of one or more nucleotides in the sequence) which do not effect (in particular impair) the yeast promoter activity. Regions that can be modified without significantly affecting the yeast promoter activity can be identified by deletion studies. A mutant promoter of the present invention has at least about 20%, preferably at least about 40%, more preferably at least about 60%, more preferably at least about 80%, more preferably at least about 90%, more preferably at least about 100%, more preferably at least about 200%, more preferably at least about 300% and most preferably at least about 400% of the promoter activity of the GPD or GPM promoter regions described herein as SEQ ID NOs:43 and 44.

Methods for mutagenesis are well known in the art and suitable for the generation of mutant promoters. For example, in vitro mutagenesis and selection, PCR based random mutagenesis, site-directed mutagenesis, or other means can be employed to obtain mutations of the naturally occurring promoters and genes of the instant invention. This would permit production of a putative promoter having a more desirable level of promoter activity in the host cell, or production of a polypeptide having more desirable physical and kinetic parameters for function in the host cell.

If desired, the regions of a nucleotide of interest important for promoter or enzymatic activity, respectively, can be determined through routine mutagenesis, expression of the resulting mutant promoters or polypeptides and determination of their activities. Mutants may include deletions, insertions and point mutations, or combinations thereof. A typical functional analysis begins with deletion mutagenesis to determine either: 1.) the minimum portion of the putative promoter necessary for activity; or 2.) the N- and C-terminal limits of the protein necessary for function. Subsequently, internal deletions, insertions or point mutants are made to further determine regions necessary for function. Other techniques such as cassette mutagenesis or total synthesis also can be used.

Deletion mutagenesis of a coding sequence is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites.

Internal deletions in a putative promoter region or within a coding sequence can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR, while point mutations are made through techniques such as site-directed mutagenesis or mutagenic PCR.

Chemical mutagenesis also can be used for identifying regions of a putative promoter region or polypeptide important for activity. A mutated construct is expressed, and the ability of the resulting altered promoter or protein, respectively, is assayed. Such structure-function analysis can determine which regions may be deleted, which regions tolerate insertions, and which point mutations allow the mutant promoter or protein to function in substantially the same way as the native promoter or protein. All such mutant promoters and nucleotide sequences encoding polypeptides that are derived from the instant promoters and genes described herein are within the scope of the present invention.

Isolation of Homologs to the qpd and gpm Genes and Putative Promoter Regions

It will be appreciated by a person of skill in the art that the promoter regions and genes of the present invention have homologs in a variety of yeast species; and, the use of the promoters and genes for heterologous gene expression are not limited to those promoters and genes derived from *Yarrowia lipolytica*, but extend to homologs in other yeast species. For example, the invention encompasses homologs derived from oleaginous genera including, but not limited to: *Yarrowia, Candida, Rhodotorula, Rhodosporidium, Cryptococcus, Trichosporon* and *Lipomyces*; examples of preferred species within these genera include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus* and *R. graminis*.

Homology typically is measured using sequence analysis software, wherein the term "sequence analysis software" refers to any computer algorithm or software program (commercially available or independently developed) that is useful for the analysis of nucleotide or amino acid sequences. In general, such computer software matches similar sequences by assigning degrees of homology to various substitutions, deletions and other modifications.

As is well known in the art, isolation of homologous promoter regions or genes using sequence-dependent protocols is readily possible using various techniques. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., Proc. Acad. Sci. USA 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, putative promoter regions or genes encoding similar proteins or polypetides to those of the instant invention could be isolated directly by using all or a portion of the instant nucleic acid molecules as DNA hybridization probes to screen libraries from any desired microbe using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation, or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis (Ed.), (1986) pp 33-50 IRL: Herndon, Va.; and Rychlik, W., In *Methods in Molecular Biology*, White, B. A. (Ed.), (1993) Vol. 15, pp 31-39, PCR Protocols: Current Methods and Applications. Humania: Totowa, N.J.).

Generally two short segments of the instant sequences may be used in polymerase chain reaction protocols to amplify longer nucleic acid molecules encoding homologous polynucleotides from DNA or RNA. The polymerase chain reaction may also be performed on a library of cloned nucleic acid molecules wherein the sequence of one primer is derived from the instant nucleic acid molecules, and the sequence of the other primer takes advantage of the presence of the polyadenylic acid tracts to the 3' end of the mRNA precursor encoding microbial genes.

Alternatively, the instant sequences may be employed as hybridization reagents for the identification of homologs. The basic components of a nucleic acid hybridization test include a probe, a sample suspected of containing the nucleotide sequence of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Recombinant Expression in Yeast

Initiation control regions or promoter regions that are useful to drive expression of a coding gene of interest in the desired host cell are selected from those derived from the upstream portion of the gpd and gpm genes (SEQ ID NOs:25 and 15, respectively). The promoter regions may be identified from the upstream sequences of gpd and gpm genes and their homologs and isolated according to common methods (Maniatis, supra). Once the promoter regions are identified and isolated, they may be operably linked to a coding region of interest to be expressed in a suitable expression vector. These chimeric genes may then be expressed in natural host cells and heterologous host cells, particularly in the cells of oleaginous yeast hosts. Thus, one aspect of the present invention provides a recombinant expression vector comprising a yeast promoter of the invention.

In a further aspect, the invention provides a method of expressing a coding region of interest in a transformed yeast cell, wherein a transformed cell is provided having a chimeric gene comprising: (i) a GPD or GPM promoter region and (ii) a coding region of interest expressible in the host, wherein the promoter region is operably linked to the coding region of interest; and the transformed cell is grown under conditions wherein the chimeric gene is expressed. The polypeptide so produced can optionally be recovered from the culture.

Microbial expression systems and expression vectors are well known to those skilled in the art. Any of these could be used to construct chimeric genes comprising the promoter regions derived from the gpm and gpd genes for production of any specific coding region of interest suitable for expression in a desirable yeast host cell. These chimeric genes could then be introduced into appropriate microorganisms by integration via transformation to provide high-level expression of the enzymes upon induction. Alternatively, the promoters can be cloned into a plasmid that is capable of transforming and replicating itself in the preferred yeast host cell. The coding region of interest to be expressed can then be cloned downstream from the promoter. Once the recombinant host is established, gene expression can be accomplished by growing the cells under suitable conditions (infra).

Suitable Coding Regions of Interest

Useful chimeric genes will include the promoter region of either of the gpd and gpm genes as defined herein or a mutant promoter thereof, operably linked to a suitable coding region of interest to be expressed in a preferred host cell.

Coding regions of interest to be expressed in the recombinant yeast host may be either endogenous to the host or heterologous and must be compatible with the host organism. Genes encoding proteins of commercial value are particularly suitable for expression. For example, suitable coding regions of interest may include (but are not limited to) those encoding viral, bacterial, fungal, plant, insect, or vertebrate coding regions of interest, including mammalian polypeptides. Further, these coding regions of interest may be, for example, structural proteins, enzymes (e.g., oxidoreductases, transferases, hydrolyases, lyases, isomerases, ligases), or peptides. A non-limiting list includes genes encoding enzymes such as aminopeptidases, amylases, carbohydrases, carboxypeptidases, catalyases, cellulases, chitinases, cutinases, cyclodextrin glycosyltransferases, deoxyribonucleases, esterases, α-galactosidases, β-glucanases, β-galactosidases, glucoamylases, α-glucosidases, β-glucosidases, invertases, laccases, lipases, mannosidases, mutanases, oxidases, pectinolytic enzymes, peroxidases, phospholipases, phytases, polyphenoloxidases, proteolytic enzymes, ribonucleases, transglutaminases or xylanases.

Preferred in the present invention in some embodiments are coding regions of the enzymes involved in the production of microbial oils, including ω-6 and ω-3 fatty acids. Many microorganisms, including algae, bacteria, molds and yeast, can synthesize PUFAs and omega fatty acids in the ordinary course of cellular metabolism. Particularly well-studied are fungi including *Schizochytrium aggregatm*, species of the genus *Thraustochytrium* and *Morteriella alpina*. Additionally, many dinoflagellates (Dinophyceaae) naturally produce high concentrations of PUFAs. As such, a variety of genes involved in oil production have been identified through genetic means and the DNA sequences of some of these genes are publicly available (e.g., see GenBank Accession No.'s AY131238, Y055118, AY055117, AF296076, AF007561, L11421, NM_031344, AF465283, AF465282, AF465281, AF110510, AF419296, AB052086, AJ250735, AF126799, AF126798, AF199596, AF226273, AF320509, AB072976, AF489588, AJ510244, AF419297, AF07879, AF067654, AB022097, AF489589.1, AY332747, MG36933, AF110509, AB020033, ML13300, AF417244, AF161219, X86736, AF240777, AB007640, AB075526, AP002063, NP_441622, BM18302, BM02924, AAL36934, AF338466, AF438199, E11368, E11367, D83185, U90417, AF085500, AY504633, NM_069854, AF230693, AX464731, NM_119617, NM_134255, NM_134383, NM_134382, NM_068396, NM_068392, NM_070713, NM_068746 and NM_064685). Additionally, the patent literature provides many additional DNA sequences of genes (and/or details concerning several of the genes above and their methods of isolation) involved in oil production. See, for example: U.S. Pat. No. 5,968,809 (Δ6 desaturases); U.S. Pat. No. 5,972,664 and U.S. Pat. No. 6,075,183 (Δ5 desaturases); WO 91/13972 and U.S. Pat. No. 5,057,419 (Δ9 desaturases); WO 93/11245 (Δ15 desaturases); WO 94/11516, U.S. Pat. No. 5,443,974 and WO 03/099216 (Δ12 desaturases); U.S. 2003/0196217 A1 (Δ17 desaturase); WO 00/12720 and U.S. 2002/0139974A1 (elongases), each of which is herein incorporated by reference in its entirety.

Components of Vectors/DNA Cassettes

Vectors or DNA cassettes useful for the transformation of suitable host cells are well known in the art. The specific choice of sequences present in the construct is dependent upon the desired expression products (supra), the nature of the host cell, and the proposed means of separating transformed cells versus non-transformed cells. Typically, however, the vector or cassette contains sequences directing transcription and translation of the relevant gene(s), a selectable marker, and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence motif to obtain optimal gene expression. For expression in yeast, this can be done by site-directed mutagenesis of an inefficiently expressed gene to include the favored translation initiation motif.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a chimeric gene into a cloning vector does not ensure that it will be successfully expressed at the level needed. In response to needs for high expression rates, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of a chimeric gene comprising a promoter region of either of the gpd and gpm genes as defined herein or a mutant promoter thereof, operably linked to a suitable coding region of interest.

Transformation of Yeast Cells

Once an appropriate chimeric gene has been constructed that is suitable for expression in a yeast cell, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other constructs to maintain stable expression and prevent reassortment of elements among constructs. Judicious choice of regulatory regions, selection means and method of propagation of the introduced construct can be experimentally determined so that all introduced genes are expressed at the necessary levels to provide for synthesis of the desired products.

Constructs comprising a coding region of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. Nos. 4,880,741 and 5,071,764 and Chen, D. C. et al. (*Appl Microbiol Biotechnol.* 48(2):232-235-(1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Preferred for use herein are resistance to kanamycin, hygromycin and the aminoglycoside G418, as well as ability to grow on media lacking uracil or leucine.

Techniques to Up-Regulate Expression of a Chimeric Gene Comprising a GPD or GPM Promoter Operably Linked to a Coding Region of Interest Additional copies a particular coding region of interest (operably linked to a promoter of the instant invention) may be introduced into the host to increase expression. Expression of the coding region of interest also can be increased by removing/deleting destabilizing sequences from either the mRNA or the encoded protein, or by adding stabilizing sequences to the mRNA (U.S. Pat. No. 4,910,141).

Yet another approach to increase expression of a coding region of interest is to increase the translational efficiency of the encoded mRNAs by replacement of codons in the native gene with those for optimal gene expression in the selected host microorganism. As will be appreciated by one skilled in the art, use of host preferred codons can substantially enhance the expression of the foreign gene encoding the polypeptide. In general, host preferred codons can be determined within a particular host species of interest by examining codon usage in proteins (preferably those expressed in the largest amount) and determining which codons are used with highest frequency. Then, the coding sequence for a polypeptide of interest can be synthesized in whole or in part using the codons preferred in the host species.

Preferred Hosts

Preferred host cells for expression of the instant genes and coding regions of interest operably linked to the instant promoter molecules herein are yeast cells (where oleaginous yeast are most preferred where the desired use is for the production of microbial oils, infra). Oleaginous yeast are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 0.82(1):43-9 (2002)). The *Y. lipolytica* strain designated as ATCC #76982 was the particular strain from which the GPD and GPM promoters and genes were isolated herein.

Industrial Production Using Transformed Yeast Expressing a Suitable Coding Region of Interest In general, media conditions which may be optimized for high-level expression of a particular coding region of interest include the type and amount of carbon source, the type and amount of nitrogen source, the carbon-to-nitrogen ratio, the oxygen level, growth temperature, pH, length of the biomass production phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon source may include one-carbon sources (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing sources and will only be limited by the choice of the host organism. Although all of the above mentioned carbon sources and mixtures thereof are expected to be suitable in the present invention, preferred carbon sources are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea or glutamate). In addition to appropriate carbon and nitrogen sources, the fermentation media must also contain suitable minerals, salts, cofactors, buffers, vitamins, and other components known to those skilled in the art suitable for the growth of the microorganism.

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Host cells comprising a suitable coding region of interest operably linked to the promoters of the present invention may be cultured using methods known in the art. For example, the cell may be cultivated by shake flask cultivation, small-scale or large-scale fermentation in laboratory or industrial fermentors performed in a suitable medium and under conditions allowing expression of the coding region of interest.

Where commercial production of a product that relies on the instant genetic chimera is desired, a variety of culture methodologies may be applied. For example, large-scale production of a specific gene product over-expressed from a recombinant host may be produced by a batch, fed-batch or continuous fermentation process.

A batch fermentation process is a closed system wherein the media composition is fixed at the beginning of the process and not subject to further additions beyond those required for maintenance of pH and oxygen level during the process. Thus, at the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high growth log phase and finally to a stationary phase, wherein the growth rate is diminished or halted. Left untreated, cells in the stationary phase will eventually die. A variation of the standard batch process is the fed-batch process, wherein the source is continually added to the fermentor over the course of the fermentation process. A fed-batch process is also suitable in the present invention. Fed-batch processes are useful when catabolite repression is apt to inhibit the metabolism of the cells or where it is desirable to have limited amounts of source in the media at any one time. Measurement of the source concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates: Sunderland, M A; or Deshpande, Mukund V., *Appl. Biochem. Biotechnol.*, 36:227 (1992), herein incorporated by reference.

Commercial production may also be accomplished by a continuous fermentation process, wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

DESCRIPTION OF PREFERRED EMBODIMENTS

Although the promoters of the present invention will be suitable for expression of any suitable coding region of interest in an oleaginous yeast, in a preferred embodiment the promoters will be utilized in the development of an oleaginous yeast that accumulates oils enriched in PUFAs. Toward this end, it is necessary to introduce and express e.g., desaturases and elongases that allow for the synthesis and accumulation of ω-3 and/or ω-6 fatty acids.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" are cis-isomers that have "double bonds" along their carbon backbones. "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "ω-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "ω-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of this disclosure, the omega-reference system will be used to indicate the number of carbons, the number of double bonds and the position of the double bond closest to the omega carbon, counting from the omega carbon (which is numbered 1 for this purpose). This nomenclature is shown below in Table 1, in the column titled "Shorthand Notation". The remainder of the Table summarizes the common names of ω-3 and ω-6 fatty acids, the abbreviations that will be used throughout the remainder of the specification, and each compounds' chemical name.

TABLE 1

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |

TABLE 1-continued

Nomenclature Of Polyunsaturated Fatty Acids

| Common Name | Abbreviation | Chemical Name | Shorthand Notation |
|---|---|---|---|
| Docosahexaenoic | DHA | cis-4,7,10,13,16,19-docosahexaenoic | 22:6 ω-3 |

Microbial Biosynthesis of Fatty Acids

In general, lipid accumulation in oleaginous microorganisms is triggered in response to the overall carbon to nitrogen ratio present in the growth medium. When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol, and subsequent cleavage of the citrate by ATP-citrate lyase to yield acetyl-CoA and oxaloacetate. Acetyl-CoA is the principle building block for de novo biosynthesis of fatty acids. The first committed step of fatty acid biosynthesis is the synthesis of malonyl-CoA, produced via carboxylation of acetyl-CoA. Fatty acid synthesis is catalyzed by a multi-enzyme fatty acid synthase complex and occurs by the condensation of eight two-carbon fragments (acetyl groups from acetyl-CoA) to form a 16-carbon saturated fatty acid, palmitate.

Palmitate is the precursor of longer chain saturated and unsaturated fatty acids (e.g., stearic (18:0), palmitoleic (16:1) and oleic (18:1) acids) through the action of elongases and desaturases present in the endoplasmic reticulum membrane. Palmitate and stearate are converted to their unsaturated derivatives, palmitoleic (16:1) and oleic (18:1) acids, respectively, by the action of a Δ9 desaturase.

Biosynthesis of Omega-3 And Omega-6 Fatty Acids

Simplistically, the metabolic process that converts LA to GLA, DGLA and ARA (the ω-6 pathway) and ALA to STA, ETA, EPA and DHA (the ω-3 pathway) involves elongation of the carbon chain through the addition of carbon atoms and desaturation of the molecule through the addition of double bonds. This requires a series of special desaturation and elongation enzymes present in the endoplasmic reticulim membrane, hereinafter referred to as "PUFA biosynthetic pathway enzymes".

More specifically, "PUFA biosynthetic pathway enzymes" will refer to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase and/or an elongase. For further clarity within the present disclosure, the term "desaturase" refers to a polypeptide component of a multi-enzyme complex that can desaturate one or more fatty acids to produce a mono- or polyunsaturated fatty acid or precursor of interest. Thus, despite use of the omega-reference system to refer to specific fatty acids, it is more convenient to indicate the activity of a desaturase by counting from the carboxyl end of the source using the delta-system. For example, a Δ17 desaturase will desaturate a fatty acid between the $17^{th}$ and $18^{th}$ carbon atom numbered from the carboxyl-terminal end of the molecule and can, for example, catalyze the conversion of ARA to EPA and/or DGLA to ETA. In contrast, the term "elongase" refers to a polypeptide component of a multi-enzyme complex that can elongate a fatty acid carbon chain to produce a mono- or polyunsaturated fatty acid that is 2 carbons longer than the fatty acid source that the elongase acts upon. This process of elongation occurs in a multi-step mechanism in association with fatty acid synthase, whereby CoA is the acyl carrier (Lassner et al., *The Plant Cell* 8:281-292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA.

Synthesis of ω-6 fatty acids occurs in the following fashion: oleic acid (the first of the ω-6 fatty acids) is converted to LA (18:2) by the action of a Δ12 desaturase (FIG. 10). Subsequent co-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase. In contrast, ω-3 fatty acids are all derived from linoleic acid (LA). Specifically: 1.) LA is converted to ALA by the action of a Δ15 desaturase; 2.) ALA is converted to STA by the activity of a Δ6 desaturase; 3.) STA is converted to ETA by the activity of an elongase; and 4.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

Production of PUFAs

As will be obvious to one skilled in the art, the particular functionalities required to be introduced into a host organism for production of a particular PUFA final product will depend on the host cell (and its native PUFA profile and/or desaturase profile), the availability of substrate and the desired end product(s). As shown in FIG. 10, LA, GLA, DGLA, ARA, ALA, STA, ETA, EPA, DPA and DHA may all be produced in oleaginous yeast, by introducing various combinations of the following PUFA enzyme functionalities: a Δ4 desaturase, a Δ5 desaturase, a Δ6 desaturase, a Δ12 desaturase, a Δ15 desaturase, a Δ17 desaturase, a Δ9 desaturase, and/or an elongase. One skilled in the art will be able to identify various candidate genes encoding each of the above enzymes, according to publicly available literature (e.g., GenBank), the patent literature, and experimental analysis of microorganisms having the ability to produce PUFAs. Thus, a variety of desaturases and elongases are suitable as coding regions of interest in the present invention. These coding regions of interest could be operably linked to the the GPD and/or GPM promoters of the present invention or mutant promoters thereof, and used as chimeric genes for expression of various ω-6 and ω-3 fatty acids, using techniques well known to those skilled in the art (see, for example co-pending U.S. patent application Ser. No. 10/840,579, herein incorporated entirely by reference). As such, the invention provides a method for the production of ω-3 and/or ω-6 fatty acids comprising:

a) providing a transformed oleaginous yeast host cell comprising a chimeric gene, comprising:

1) a promoter region of a gene selected from the group consisting of: the promoter region of a gpm gene and the promoter region of a gpd gene; and 2) a coding region of interest expressible in the oleaginous yeast encoding an enzyme of a functional ω-3/ω-6 fatty acid biosynthetic pathway;

wherein the promoter region and coding region are operably linked; and (b) contacting the host cell of step (a) under suitable growth conditions whereby one or more ω-3 or ω-6 fatty acids are produced.

In preferred embodiments, the nucleic acid sequence of the promoter region is selected from the group consisting of: SEQ ID NOs:23, 27, 43 and 44, and subsequences and mutant promoters thereof; and the coding region of interest is any desaturase or elongase suitable for expression in the oleaginous yeast for the production of ω-3 or ω-6 fatty acids.

For production of the greatest and the most economical yield of PUFAs, the transformed oleaginous yeast host cell is grown under conditions that optimize desaturase and elongase activities by optimizing expression of the chimeric genes of the present invention, wherein these chimeric genes comprise a promoter region of a gpm or gpd gene and a coding region of interest encoding a PUFA biosynthetic pathway enzyme.

In the fermentation media, particular attention is given to several metal ions (e.g., $Mn^{+2}$, $Co^{+2}$, $Zn^{+2}$, $Mg^{+2}$) that promote synthesis of lipids and PUFAs (Nakahara, T. et al. *Ind. Appl. Single Cell Oils*, D. J. Kyle and R. Colin, eds. pp 61-97 (1992)).

The preferred "fermentable carbon source" for production of oleaginous yeast expressing various ω-6 and ω-3 fatty acids will include, but is not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of oil. Although cells are typically grown at about 30° C., some studies have shown increased synthesis of unsaturated fatty acids at lower temperatures (Yongmanitchai and Ward, *Appl. Environ. Microbiol.* 57:419-25 (1991)). Based on process economics, this temperature shift should likely occur after the first phase of the two-stage fermentation, when the bulk of the organisms' growth has occurred.

Purification of PUFAs

The PUFAs produced in a host microorganism as described herein may be found as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical*

Reviews in Biotechnology 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification, and physical means such as presses, or combinations thereof. Of particular interest is extraction with methanol and chloroform in the presence of water (E. G. Bligh & W. J. Dyer, *Can. J. Biochem. Physiol.* 37:911-917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation or iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (hereinafter "Maniatis"); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

A leucine autotrophic strain of *Yarrowia lipolytica* was purchased from the American Type Culture Collection (Rockville, Md.; ATCC #76982) and used for functional assays. *Y. lipolytica* strains were usually grown at 2° C. on YPD agar (1% yeast extract, 2% bactopeptone, 2% glucose, 2% agar). For selection of transformants, minimal medium (0.17% yeast nitrogen base (DIFCO Laboratories) without ammonium sulfate or amino acids, 2% glucose, 0.1% proline, pH 6.1) was used. Supplements of adenine, leucine, lysine and/or uracil were added to a final concentration of 0.01%.

General molecular cloning was performed according to standard methods (Sambrook et al., supra). Oligonucleotides were synthesized by Sigma-Genosys (Spring, Tex.). Site-directed mutagenesis was performed using Stratagene's QuikChange™ Site-Directed Mutagenesis kit (San Diego, Calif.), per the manufacturer's instructions. When polymerase chain reaction (PCR) or site-directed mutagenesis was involved in subcloning, the constructs were sequenced to confirm that no errors had been introduced to the sequence. PCR products were cloned into Promega's pGEM-T-easy vector (Madison, Wis.).

Manipulations of genetic sequences were accomplished using the suite of programs available from the Genetics Computer Group Inc. (Wisconsin Package Version 9.0, Genetics Computer Group (GCG), Madison, Wis.). The GCG program "Pileup" was used with the gap creation default value of 12, and the gap extension default value of 4. The GCG "Gap" or "Bestfit" programs were used with the default gap creation penalty of 50 and the default gap extension penalty of 3. Unless otherwise stated, in all other cases GCG program default parameters were used.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Example 1

Isolation of a Portion of the *Yarrowia lipolytica* GPD

The present Example describes the identification of a portion of the *Yarrowia lipolytica* gene encoding GPD (SEQ ID NOs:11 and 12), by use of primers derived from conserved regions of other GPD sequences.

A comparison of the various protein sequences encoding GPD genes from *Saccharomyces cerevisiae* (GenBank Accession No. CAA24607; SEQ ID NO:1), *Schizosaccharomyces pombe* (GenBank Accession No. NP_595236; SEQ ID NO:2), *Aspergillus oryzae* (GenBank Accession No. AAK08065; SEQ ID NO:3), *Paralichthys olivaceus* (GenBank Accession No. BAA88638; SEQ ID NO:4), *Xenopus*

Figure 1A:
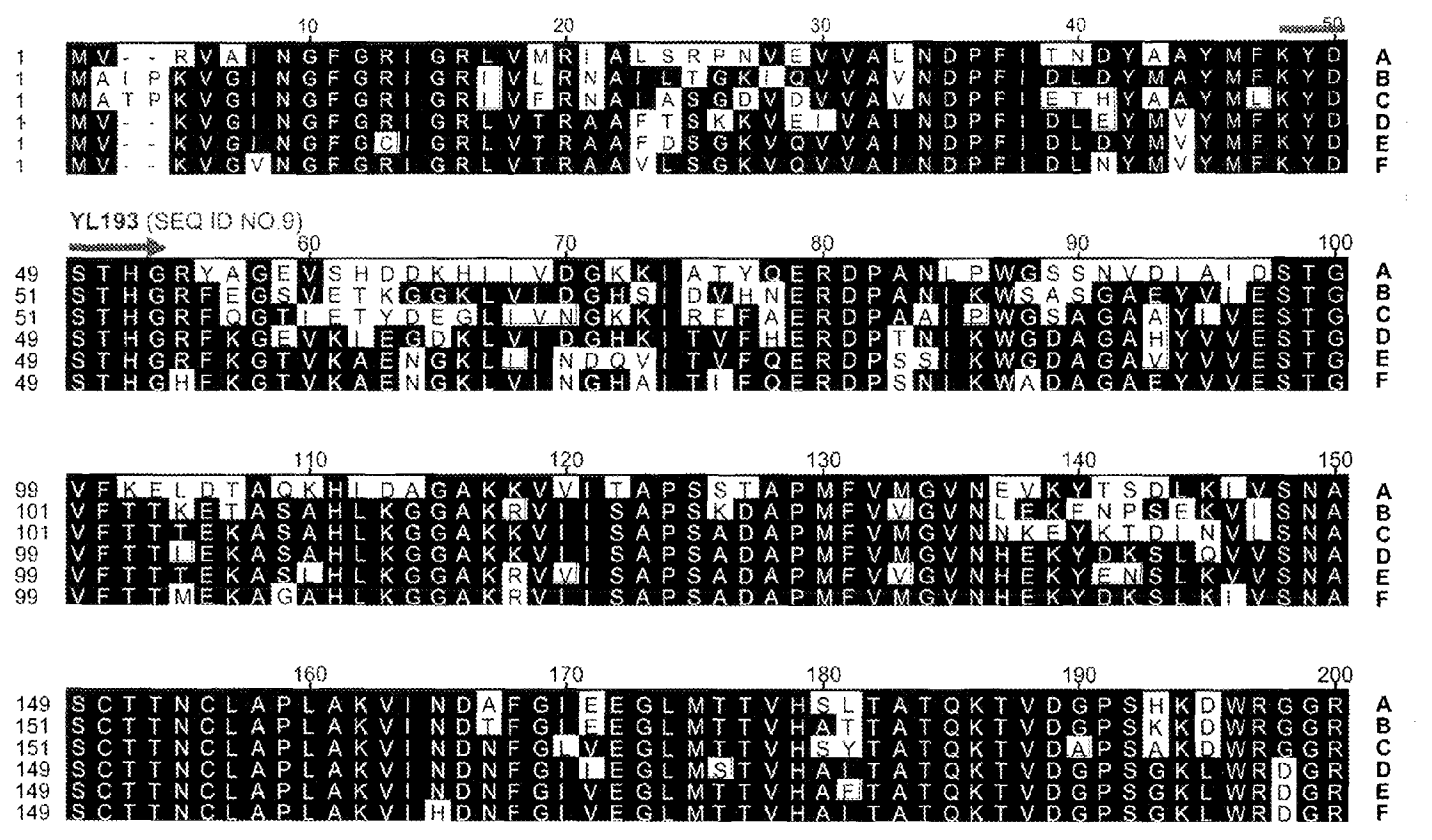

*laevis* (GenBank Accession No. P51469; SEQ ID NO:5), and *Gallus gallus* (GenBank Accession No. DECHG3; SEQ ID NO:6) showed that there were several stretches of conserved amino acid sequence between the 6 different organisms (FIGS. 1A and 1B). Thus, two degenerate oligonucleotides (shown below), corresponding to the conserved 'KYDSTHG' (SEQ ID NO:7) and 'TGAAKAV' (SEQ ID NO:8) amino acid sequences, respectively, were designed and used to amplify a portion of the coding region of GPD from *Y. lipolytica*:

```
Degenerated oligonucleotide YL193
AAGTACGAYTCBACYCAYGG                    (SEQ ID NO:9)

Degenerated oligonucleotide YL194
ACRGCCTTRGCRGCDCCRGT                    (SEQ ID NO:10)

[Note:
The nucleic acid degeneracy code used for SEQ ID
NOs:9 and 10 was as follows: R = A/G; Y = C/T; B =
C/G/T; and D = A/G/T.]
```

Based on the full-length sequences of the GPD sequences of FIG. 1, it was hypothesized that the *Yarrowia lipolytica* GPD gene amplified as described above would be missing ~50 amino acids from its N-terminus and about ~115 amino acids from its C-terminus.

The PCR amplification was carried out in a 50 µl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer, 50 ng genomic DNA of *Y. lipolytica* (ATCC #76982) and 1 µl of Taq DNA polymerase (Epicentre Technologies). The thermocycler conditions were set for 35 cycles at 95° C. for 1 min, 56° C. for 30 sec, and 72° C. for 1 min, followed by a final extension at 72° C. for 10 min.

The PCR products were purified using a Qiagen PCR purification kit (Valencia, Calif.), and then further purified following gel electrophoresis in 1% (w/v) agarose. Subsequently, the PCR products were cloned into the pGEM-T-easy vector (Promega, Madison, Wis.). The ligated DNA was used to transform cells of *E. coli* DH5α and transformants were selected on LB agar containing ampicillin (100 µg/mL). Analysis of the plasmid DNA from one transformant confirmed the presence of a plasmid of the expected size, and designated as "pT-GPD".

Sequence analyses showed that pT-GPD contained a 507 bp fragment (SEQ ID NO:11). Identity of this sequence was determined by conducting BLAST (Basic Local Alignment Search Tool; Altschul, S. F., et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). Similarity to all publicly available DNA sequences contained in the "nr" database was determined using the BLASTN algorithm provided by the National Center for Biotechnology Information (NCBI). The DNA sequence was translated in all reading frames and compared for similarity to all publicly available protein sequences contained in the "nr" database, using the BLASTX algorithm (Gish, W. and States, D. J. *Nature Genetics* 3:266-272 (1993)) provided by the NCBI. The results of the BLAST comparison summarizing the sequence to which SEQ ID NO:11 has the most similarity are reported according to the % identity, % similarity, and Expectation value. "% Identity" is defined as the percentage of amino acids that are identical between the two proteins. % Similarity" is defined as the percentage of amino acids that are identical or conserved between the two proteins. "Expectation value" estimates the statistical significance of the match, specifying the number of matches, with a given score, that are expected in a search of a database of this size absolutely by chance.

The 507 bp of pT-GPD was found to encode 169 amino acids (SEQ ID NO:12). This amino acid fragment had 77% identity and 84% similarity (FIG. 2) with the GPD protein sequence of fission yeast (GenBank Accession No. NP_595236), with an expectation value of 6e-68. The *Yarrowia* sequence possessed the 'KYDSTHG' (SEQ ID NO:7) and 'TGMKAV' (SEQ ID NO:8) amino acid sequences (corresponding to the degenerate primers used to amplify the fragment) at its N- and C-termini. Further sequence comparison of this partial GPD sequence determined that it also shared about 72% and 74% identity with the GPD proteins from chick (GenBank Accession No. DECHG3) and frog (GenBank Accession No. P51469), respectively (FIG. 2).

Example 2

Identification of the *Yarrowia lipolytica* GPM

The present Example describes the identification of the *Yarrowia lipolytica* gene encoding GPM, by use of a *S. cerevisiae* GPM protein sequence as a query sequence against a *Y. lipolytica* genomic database.

Specifically, the *S. cerevisiae* GPM protein sequence (GenBank Accession No. NP_012770; SEQ ID NO:13) was used in BLAST searches (as described in Example 1) against the public *Y. lipolytica* database of the "Yeast project Genolevures" (Center for Bioinformatics, LaBR1, Talence Cedex, France.

One contig ("Contig 2217"; SEQ ID NO:14) was identified that encoded GPM in *Y. lipolytica*. Contig 2217 is 1049 bp in length, although 5 nucleotide positions had ambiguous sequence (having an "n" at nucleotide position 1020, "y" at positions 39, 62, 331; and a "m" at position 107). The DNA sequence of Contig 2217 was translated in all reading frames and compared for similarity to all publicly available protein sequences contained in the "nr" database using the BLASTX algorithm (as described in Example 1). Based on these DNA and protein sequence analyses, it was determined that:

The GPM translation initiation codon 'ATG' was at bp 388 within SEQ ID NO:14; thus, Contig 2217 possessed about 388 bp upstream sequence relative to the 'ATG' codon; and Contig 2217 was missing one base at nucleotide position 470, which resulted in a frame shift.

The deduced coding region sequence of GPM that corresponded to Contig 2217 was 651 bp in length (SEQ ID NO:15) and the protein sequence was encoded by SEQ ID NO:16. This 216 amino acid protein had 71% identity, 82% similarity, and an expectation value of 3e-81 with the GPM protein sequence of *S. cerevisiae* (GenBank Accession No. NP_012770; Goffeau, A., et al., *Science* 274(5287): 546 (1996)) (FIG. 3).

Example 3

Isolation of the 5' Upstream Regions of the qpd and qpm Genes from *Yarrowia lipolytica*

To isolate the GPD and GPM promoter regions from the genes identified in Examples 1 and 2, a genome-walking technique (TOPO® Walker Kit, Invitrogen, CA) was utilized.

Briefly, genomic DNA of *Y. lipolytica* was digested with KpnI, SacI, SphI or PacI, and dephosphorylated with Calf Intestinal Alkaline Phosphatase (CIP), separately. Primer extension reactions were then carried out individually using the dephosphorylated DNA as template and one of the following oligonucleotides as primer: YL206 (SEQ ID NO:17) for GPD and YL196 (SEQ ID NO:18) for GPM. The primer extended products were linked with TOPO® linker and used as templates for the first PCR reactions using primers of LinkAmp Primer1 and a second appropriate oligonucleotide. Specifically, YL207 (SEQ ID NO:19) was used as the second primer targeted for the upstream promoter region of GPD and YL197 (SEQ ID NO:20) was used as the second primer for PCR reactions targeted to the upstream GPM promoter region. The PCR amplifications were carried out in a 50 μl total volume, comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer and 1 μl of Taq DNA polymerase (Epicentre Technologies). The thermocycler conditions were set for 35 cycles at 95° C. for 1 min, 56° C. for 30 sec, and 72° C. for 1 min, followed by a final extension at 72° C. for 10 min.

Second PCR reactions were then carried out using the first PCR product as template and primers of LinkAmp primer 2 and the appropriate oligonucleotide. Specifically, the first PCR product for GPD was used as template in a reaction comprising LinkAmp primer 2 and YL208 (SEQ ID NO:21); in contrast, the first PCR product for GPM was used as template in a reaction comprising LinkAmp primer 2 and YL198 (SEQ ID NO:22). The PCR amplifications were carried out as described above.

The PCR products comprising the 5' upstream regions of the GPD and GPM genes were each individually purified using a Qiagen PCR purification kit, followed by gel electrophoresis in 1% (w/v) agarose. Products were then cloned into the pGEM-T-easy vector (Promega, Madison, Wis.). The ligated DNA was used to transform *E. coli* DH5α and transformants were selected on LB agar containing ampicillin (100 μg/mL).

Analysis of the plasmid DNA from one transformant comprising the 5' upstream region of the gpd gene confirmed the presence of the expected plasmid, designated "pT-GPDP". Sequence analyses showed that pT-GPDP contained a fragment of 1848 bp (SEQ ID NO:23), which included 1525 bp of 5' upstream sequence from the nucleotide 'A' (designated as +1) of the translation initiation codon 'ATG' of the GPD gene. A complete assembly of overlapping SEQ ID NOs:23 and 11 yielded a single contig comprising 1525 bp upstream of the GPD initiation codon and 791 bp of the gene (SEQ ID NO:24; FIG. 4). Further analysis of the partial gene sequence (+1 to +791) revealed the presence of an intron (base pairs +49 to +194). Thus, the partial cDNA sequence encoding the GPD gene in *Y. lipolytica* is only 645 bp in length (SEQ ID NO:25) and the corresponding protein sequence (SEQ ID NO:26) is 215 amino acids. The protein was compared via BLAST analysis for similarity to all publicly available protein sequences (as described in Example 1). Based on this analysis, it was determined that the partial GPD protein was most similar to the GPD of *Cryotococcus cyrvatus* (GenBank Accession No's Q9Y796 and AAD25080) (81% identical).

Analysis of the plasmid DNA from one transformant comprising the the 5' upstream region of the gpm gene confirmed the presence of the expected plasmid, designated "pT-GPML". Sequence analyses showed that pT-GPML contained a fragment of 953 bp (SEQ ID NO:27). This clone possessed 875 bp of 5' upstream sequence from the translation initiation codon of the GPM gene. Assembly of DNA corresponding to overlapping SEQ ID NOs:27 and 15 yielded a single contig of DNA represented as SEQ ID NO:28 (FIG. 5). This contig therefore contained the −875 to +662 region of the GPM gene, wherein the 'A' position of the 'ATG' translation initiation codon was designated as +1.

Example 4

Synthesis of pY5-30

The present Example describes the synthesis of pY5-30, comprising a TEF::GUS::XPR chimeric gene. This was required for comparative studies investigating the promoter activity of TEF, GPD and GPM, wherein constructs comprising each promoter and a reporter gene were prepared and analyzed (Examples 5-7). Specifically, the reporter was the *E. coli* gene encoding β-glucuronidase (GUS; Jefferson, R. A. *Nature*. 342(6251):837-838 (1989)).

Amplification of the GUS Coding Region

The GUS coding region was amplified using pBI101 (Jefferson, R. A et al., *EMBO J.* 6:3901-3907 (1987)) as template and oligonucleotides YL33 (SEQ ID NO:29) and YL34 (SEQ ID NO:30) as primers. The PCR amplification was carried out in a 50 μl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer and 1 μl of Pfu DNA polymerase (Stratagene, San Diego, Calif.). The thermocycler conditions were set for 35 cycles at 95° C. for 1 min, 56° C. for 30 sec, 72° C. for 1 min, followed by a final extension at 7° C. for 10 min. The PCR products were digested with NcoI and PacI.

Synthesis of Plasmid pY5-10

The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in *Yarrowia lipolytica*, as diagrammed in FIG. 6. The partially-digested 3598 bp EcoRI fragment containing the ARS18 sequence and LEU2 gene of pINA532 was subcloned into the EcoRI site of pBluescript (Strategene, San Diego, Calif.) to generate pY2.

The TEF promoter (Muller S., et al. Yeast, 14:1267-1283 (1998)) was amplified from *Y. lipolytica* genomic DNA by PCR using TEF5' (SEQ ID NO:31) and TEF3' (SEQ ID NO:32) as primers. PCR amplification was carried out in a 50 μl total volume containing: 100 ng *Yarrowia* genomic DNA, PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer and 1 μl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 418 bp PCR product was ligated into pCR-Blunt to generate pIP-tef. The BamHI/EcoRV fragment of pIP-tef was subcloned into the BamHI/SmaI sites of pY2 to generate pY4.

The XPR2 transcriptional terminator was amplified by PCR using pINA532 as template and XPR5' (SEQ ID NO:33) and XPR3' (SEQ ID NO:34) as primers. The PCR amplification was carried out in a 50 µl total volume, using the components and conditions described above. The 179 bp PCR product was digested with SacII and then ligated into the SacII site of pY4 to generate pY5. Thus, pY5 (shown in FIG. 6) contained: a Yarrowia autonomous replication sequence (ARS18); a ColE1 plasmid origin of replication; an ampicillin-resistance gene (AmpR) for selection in E. coli; a Yarrowia LEU2 gene encoding isopropylmalate isomerase, for selection in Yarrowia; the translation elongation promoter ("TEF P"), for expression of heterologous genes in Yarrowia; and the extracellular protease gene terminator (XPR2) for transcriptional termination of heterologous gene expression in Yarrowia.

Figure 7A:
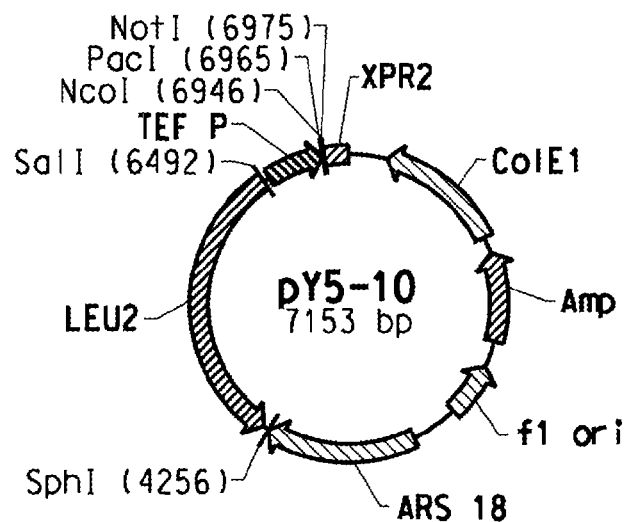
Figure 7B:
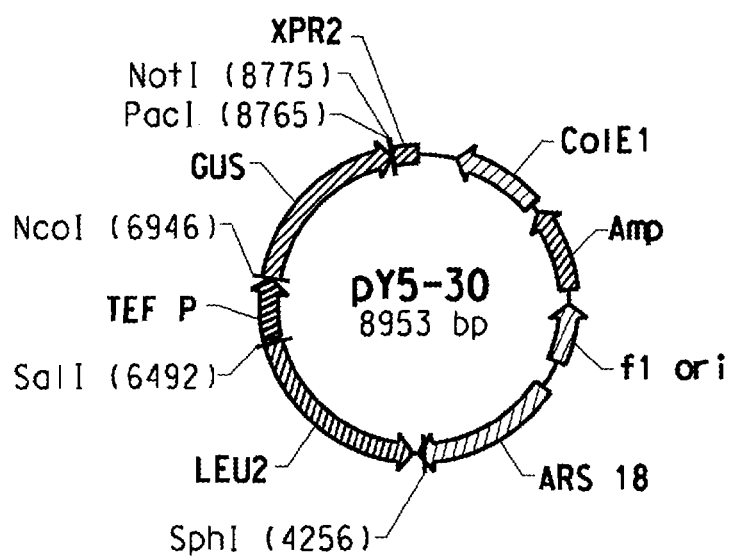

Plasmid pY5-10 (FIG. 7A) was constructed as a derivative of pY5. First, pY5-4 (FIG. 6) was constructed by three rounds of site-directed mutagenesis using pY5 as template. A NcoI site located inside the LEU2 reporter gene was eliminated from pY5 using oligonucleotides YL1 and YL2 (SEQ ID NOs:35 and 36) to generate pY5-1. A NcoI site was introduced into pY5-1 between the TEF promoter and XPR transcriptional terminator by site-directed mutagenesis using oligonucleotides YL3 and YL4 (SEQ ID NOs:37 and 38) to generate pY5-2. A PacI site was then introduced into pY5-2 between the TEF promoter and XPR transcriptional terminator using oligonucleotides YL23 and YL24 (SEQ ID NOs:39 and 40) to generate pY54. Finally, a SalI site was introduced into pY5-4 between the TEF promoter and the LEU2 gene by site-directed mutagenesis using oligonucleotides YL9 (SEQ ID NO:41) and YL10 (SEQ ID NO:42) as primers to generate pY5-10 (FIG. 7A).

Synthesis of Plasmid pY5-30

Plasmid pY5-30 (FIG. 7B), comprising a TEF::GUS::XPR chimeric gene, was synthesized by inserting the NcoI/PacI PCR product comprising the GUS coding region (supra) into NcoI/PacI digested pY5-10.

Example 5

Synthesis of pYZGDG and pYZGMG

The present Example describes the synthesis of PYZGDG (comprising a GPD::GUS::XPR chimeric gene) and PYZGMG (comprising a GPM::GUS::XPR chimeric gene). Synthesis of these plasmids first required identification and amplification of the putative GPD and GPM promoter regions. Then, each putative promoter region was cloned into a derivative of pY5-30.

Identification and Amplification of Putative Promoter Regions

After the isolation of the 5' upstream sequence of the GPD and GPM genes by genome walking, the translation start site was identified by looking for the consensus motif around the translation initiation 'ATG' codon and by comparison of the translated coding region of the Yarrowia GPD and GPM genes with the GPD and GPM genes, respectively, from other organisms. The region upstream of the genes' 'ATG' start site was used to identify putative promoter regions.

Thus, the nucleotide region between the −968 position and the 'ATG' translation initiation site of the GPD gene (wherein the 'A' nucleotide of the 'ATG' translation initiation codon was designated as +1) was determined to contain the putative promoter region ("GPDPro", provided as SEQ ID NO:43). In like manner, the nucleotide region between the −875 position and the 'ATG' translation initiation site of the GPM gene was determined to contain the putative promoter region ("GPMLPro", provided as SEQ ID NO:44).

The putative promoter regions identified above were amplified by PCR. Specifically, GPDPro was amplified with oligonucleotides YL211 (SEQ ID NO:45) and YL212 (SEQ ID NO:46) as primers and pT-GPDP (Example 3) as template. GPMLPro was amplified with oligonucleotides YL203 (SEQ ID NO:47) and YL204 (SEQ ID NO:48) as primers and pT-GPML (Example 3) as template. The PCR amplifications were carried out in a 50 µl total volume, comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.). The thermocycler conditions were set for 35 cycles at 95° C. for 1 min, 56° C. for 30 sec, 7° C. for 1 min, followed by a final extension at 72° C. for 10 min.

The PCR products were then purified using a Qiagen PCR purification kit and subjected to the following restriction digestions and ligation reactions:

GPDPro was completely digested with SalI and then partially digested with NcoI. The SalI/NcoI fragment was purified following gel electrophoresis in 1% (w/v) agarose and ligated to NcoI/SalI digested pY5-30 vector (Example 4) (wherein the NcoI/SalI digestion had excised the TEF promoter from the pY5-30 vector backbone).

GPMLPro was digested with NcoI and SalI for 1 hr at 3° C. and then purified following gel electrophoresis in 1% (w/v) agarose. The NcoI/SalII-digested PCR product was ligated to NcoI/SalI digested pY5-30 vector.

Ligated DNA from each reaction was then used to individually transform E. coli DH5α. Transformants were selected on LB agar containing ampicillin (100 µg/mL).

Figure 7C:
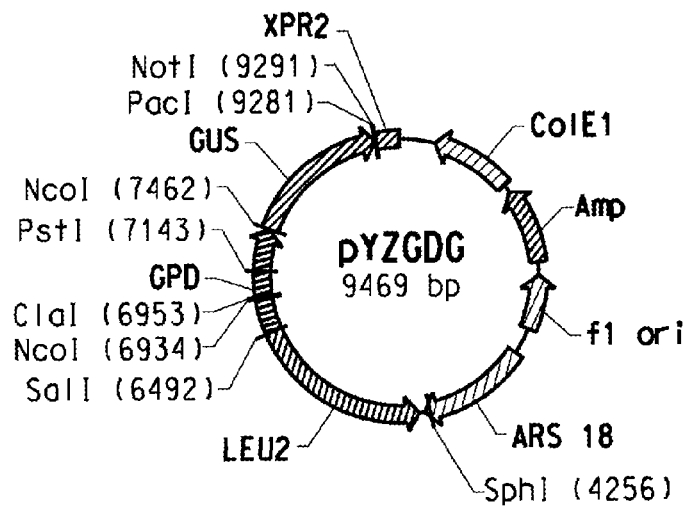

Analysis of the plasmid DNA from one transformant containing GPDPro confirmed the presence of the expected plasmid, designated "pYZGDG" (FIG. 7C). Thus, this plasmid contained a chimeric gene comprising a GPD promoter, GUS reporter gene and XPR terminator.

Figure 7D:
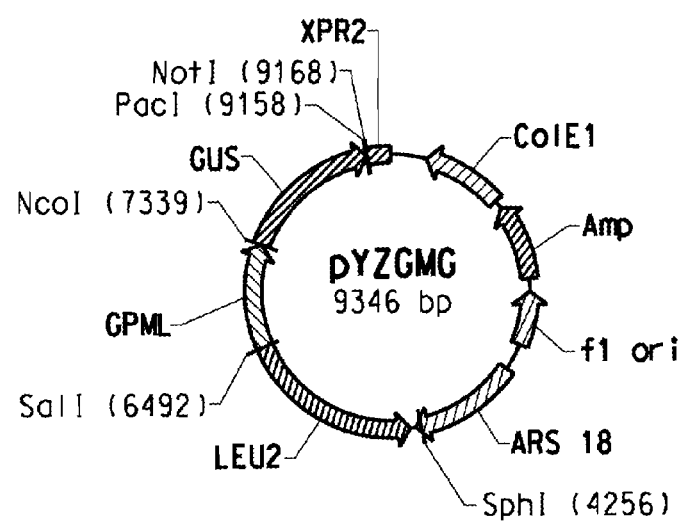

Analysis of the plasmid DNA from one transformant containing GPMLPro confirmed the presence of the expected plasmid, designated "pYZGMG", and comprising a GPM::GUS::XPR chimeric gene (FIG. 7D).

Example 6

Transformation of Y. lipolytica with pY5-30. pYZGDG and pYZGMG

The plasmids pY5-30 (Example 4; comprising a TEF::GUS::XPR chimeric gene), pYZGDG (Example 5; comprising a GPD::GUS::XPR chimeric gene) and pYZGMG (Example 5; comprising a GPM::GUS::XPR chimeric gene) were transformed separately into Y. lipolytica ATCC #76982 according to the method of Chen, D. C. et al. (*Appl. Microbiol Biotechnol.* 48(2):232-235 (1997)).

Briefly, a leucine auxotroph of *Yarrowia* was streaked onto a YPD plate and grown at 3° C. for approximately 18 hr. Several large loopfuls of cells were scraped from the plate and resuspended in 1 mL of transformation buffer containing:

2.25 mL of 50% PEG, average MW 3350;
0.125 mL of 2 M Li acetate, pH 6.0;
0.125 mL of 2 M DTT; and
50 μg sheared salmon sperm DNA.

About 500 ng of plasmid DNA was incubated in 100 μl of resuspended cells, and maintained at 39° C. for 1 hr with vortex mixing at 15 min intervals. The cells were plated onto minimal media plates lacking leucine and maintained at 30° C. for 2 to 3 days.

Using this technique, transformants were obtained that contained pY5-30, pYZGDG and pYZGMG, respectively.

Example 7

Comparative Analysis of the TEF, GPD and GPM Promoter Activities in *Yarrowia lipolytica*

The activity of the TEF, GPD and GPM promoters were determined in *Yarrowia lipolytica* containing the pY5-30, PYZGDG and pYZGMG constructs, each of which possessed a GUS reporter gene and an XPR terminator. GUS activity in each expressed construct was measured by histochemical and fluorometric assays (Jefferson, R. A. *Plant Mol. Biol. Reporter* 5:387-405 (1987)).

GUS Activities, Determined by Histochemical Assay

Specifically, two *Yarrowia lipolytica* strains containing plasmid pY5-30, two *Yarrowia lipolytica* strains containing plasmid pYZGDG and two *Yarrowia lipolytica* strains containing plasmid pYZGMG were each grown from single colonies in 3 mL minimal media (20 g/L glucose, 1.7 g/L yeast nitrogen base without amino acids, 1 g/L L-proline, 0.1 g/L L-adenine, 0.1 g/L L-lysine, pH 6.1) at 30° C. to an $OD_{600}$~1.0. Then, 100 μl of cells were collected by centrifugation, resuspended in 100 μl of histochemical staining buffer and incubated at 30° C. [Staining buffer prepared by dissolving 5 mg of 5-bromo-4-chloro-3-indolyl glucuronide (X-Gluc) in 50 μl dimethyl formamide, followed by addition of 5 mL 50 mM $NaPO_4$, pH 7.0.]

The results of histochemical staining showed that the TEF promoter in construct pY5-30, the GPD promoter in construct pYZGDG and the GPM promoter in construct pYZGMG were all active. The GPD promoter appeared to be much stronger than the TEF promoter (FIG. 8A), while the GPM promoter was at least as strong as the TEF promoter (FIG. 8B).

GUS Activities, Determined by Fluorometric Assay

GUS activity was also assayed by fluorometric determination of the production of 4-methylumbelliferone from the corresponding substrate β-glucuronide (Jefferson, R. A., supra).

*Yarrowia lipolytica* strains containing plasmids pY5-30, pYZGDG and pYZGMG, respectively, were grown from single colonies in 3 mL minimal media (as described above) at 30° C. to an $OD_{600}$~1.0. Then, the 3 mL cultures were each added to a 500 mL flask containing 50 mL minimal media and grown in a shaking incubator at 30° C. for about 24 hrs. The cells were collected by centrifugation, resuspended in Promega Cell Lysis Buffer and lysed using the BIO 101 Biopulverizer system (Vista, Calif.). After centrifugation, the supernatants were removed and kept on ice.

For each fluorometric assay, 100 μl of extract was added to 700 μl of GUS assay buffer (2 mM 4-methylumbelliferyl-β-D-glucuronide ("MUG") in extraction buffer) and placed at 37° C. Aliquots of 100 μl were taken at 0, 30 and 60 min time points and added to 900 μl of stop buffer (1 M $Na_2CO_3$). Each time point was read using a Fluorimeter (CytoFluor R Series 4000, Framingham, Mass.) set to an excitation wavelength of 360 nm and an emission wavelength of 455 nm. Total protein concentration of each sample was determined using 10 μl of extract and 200 μl of BiORad Bradford reagent (Bradford, M. M. *Anal. Biochem.* 72:248-254 (1976)). GUS activity was expressed as nmoles of 4-MU per minute per mg of protein.

Results of these fluorometric assays are shown in FIG. 9. Specifically, FIG. 9A showed that the GPD promoter was 3 times stronger than the bench-marker TEF promoter in *Y. lipolytica*; in contrast, FIG. 9B showed that the GUS activity of the GPM promoter was about 110% as active as the bench-marker TEF promoter.

Example 8

Use of the GPD Promoter for Δ15 Desaturase Expression in *Yarrowia lipolytica*

The present Example describes the construction of a chimeric gene comprising a GPD promoter, fungal Δ15 desaturase and the XPR terminator, and the expression of this gene in *Y. lipolytica*. Since transformed host cells were able to produce ALA (while wildtype *Y. lipolytica* do not possess any Δ15 desaturase activity), this confirms the ability of the GPD promoter to drive expression of heterologous PUFA biosynthetic pathway enzymes in oleaginous yeast cells such as *Y. lipolytica*.

Construction of Plasmid pY34, Comprising a GPD::Fm1:: XPR Chimeric Gene

First, plasmid pY5-13 was constructed as a derivative of pY5 (from Example 4). Specifically, pY5-13 was constructed by 6 rounds of site-directed mutagenesis using pY5 as template. Both SalI and ClaI sites were eliminated from pY5 by site-directed mutagenesis using oligonucleotides YL5 and YL6 (SEQ ID NOs:49 and 50) to generate pY5-5. A SalI site was introduced into pY5-5 between the LEU2 gene and the TEF promoter by site-directed mutagenesis using oligonucleotides YL9 and YL10 (SEQ ID NOs:41 and 42) to generate pY5-6. A PacI site was introduced into pY5-6 between the LEU2 gene and ARS18 using oligonucleotides YL7 and YL8 (SEQ ID NOs:51 and 52) to generate pY5-8. A NcoI site was introduced into pY5-8 around the translation start codon of the TEF promoter using oligonucleotides YL3 and YL4 (SEQ ID NOs:37 and 38) to generate pY5-9. The NcoI site inside the LEU2 gene of pY5-9 was eliminated using YL1 and YL2 oligonucleotides (SEQ ID NOs:35 and 36), to generate pY5-12. Finally, a BsiWI site was introduced into pY5-12 between the ColEI and XPR region using oligonucleotides YL61 and YL62 (SEQ ID NOs:53 and 54) to generate pY5-13.

A purified SalI/NcoI fragment comprising GPDPro (from Example 5) was ligated to NcoI/SalI digested pY5-13 vector (wherein the NcoI/SalI digestion had excised the TEF promoter from the pY5-13 vector backbone) to yield "pY5-13GPD". Thus, pY5-13GPD comprised a GPD promoter:: XPR terminator expression cassette.

The Nco I site at the 3' end of the promoter fragment in pY5-13GPD was converted to a Not I site to yield "pY5-

13GPDN". For this, the GPD promoter was re-amplified by PCR using GPDsense (SEQ ID NO:55) and GPDantisense (SEQ ID NO:56) primers with a Not site. The resultant promoter fragment was digested with Sal and Not and cloned into the Sal/NotI site of pY5-13 (thus removing the TEF promoter) to produce pY5-13GPDN.

The ORF encoding the *Fusarium moniliforme* strain M-8114 Δ15 desaturase (SEQ ID NO:57; see co-pending U.S. Provisional Application No. 60/519,191) was PCR amplified using the cDNA clone ffm1c.pK001.g23 (E.I. du Pont de Nemours and Co., Inc., Wilmington, Del.) containing the full-length cDNA as the template and using upper and lower primers P192 (SEQ ID NO:59) and P193 (SEQ ID NO:60). The PCR was carried out in an Eppendorf Mastercycler Gradient Cycler using Pfu polymerase, per the manufacturer's recommendation. Amplification was carried out as follows: initial denaturation at 95° C. for 1 min, followed by 30 cycles of denaturation at 95° C. for 30 sec, annealing at 5° C. for 1 min, and elongation at 72° C. for 1 min. A final elongation cycle at 72° C. for 10 min was carried out, followed by reaction termination at 4° C.

The correct-sized (ca. 1240 bp) fragment was obtained, purified from an agarose gel using a Qiagen DNA purification kit, digested with Not I and cloned into the Not I site between the GPD promoter and XPR terminator of plasmid pY5-13GPDN. This resulted in creation of plasmid "pY34", which contained a GPD::Fm1::XPR chimeric gene.

Expression of Plasmid pY34 (GPD::Fm1::XPR) in *Yarrowia lipolytica* pY5 (vector alone control, from Example 4) and pY34 (GPDP::Fm1::XPR) were each individually transformed into wild type (WT) *Yarrowia lipolytica* ATCC #76892, using the transformation procedure described in Example 6, and selected on Bio101 DOB/CSM-Leu plates.

Single colonies of wild type and transformant cells were each grown in 3 mL minimal media (formulation/L: 20 g glucose, 1.7 g yeast nitrogen base, 1 g L-proline, 0.1 g L-adenine, 0.1 g L-lysine, pH 6.1) at 30° C. to an $OD_{600}$~1.0. The cells were harvested, washed in distilled water, speed vacuum dried and subjected to direct transesterification and GC analysis. Specifically, for fatty acid analysis cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G., and Nishida I. Arch Biochem Biophys. 276(1):3846 (1990)) and subsequently analyzed with a Hewlett-Packard 6890 GC fitted with a 30-m×0.25 mm (i.d.) HP—INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

The fatty acid profile of wildtype *Yarrowia* and each of the transformants are shown below in Table 2. Fatty acids are identified as 16:0 (palmitate), 16:1 (palmitoleic acid), 18:0, 18:1 (oleic acid), 18:2 (LA) and 18:3 (ALA) and the composition of each is presented as a % of the total fatty acids.

TABLE 2

Expression of *Fusarium* Δ15 Desaturase In *Yarrowia lipolytica*

| *Y. lipolytica* strain | % 16:0 | % 16:1 | % 18:0 | % 18:1 | % 18:2 | % ALA |
|---|---|---|---|---|---|---|
| WT | 12 | 9 | 1 | 34 | 44 | 0 |
| WT + GPD:Fm1:XPR | 10 | 10 | 1 | 37 | 7 | 31 |

The results above demonstrated that the GPD promoter is suitable to drive expression of the Δ15 desaturase, leading to production of ALA in *Yarrowia*.

What is claimed is:

1. An isolated nucleic acid molecule comprising a gpd promoter as set forth in SEQ ID NO:43.

* * * * *